US008986687B2

(12) United States Patent
Martin-Vilalba et al.

(10) Patent No.: US 8,986,687 B2
(45) Date of Patent: Mar. 24, 2015

(54) COMPOUNDS INHIBITING CD95 SIGNALING FOR THE TREATMENT OF PANCREATIC CANCER

(75) Inventors: Ana Martin-Vilalba, Heidelberg (DE); Peter Herhaus, Heidelberg (DE); Ignacio Sancho-Martinez, La Jolla, CA (US); Susanne Kleber, Heidelberg (DE); Thilo Welsch, Heidelberg (DE)

(73) Assignees: Deutsches Krebsforschungszentrum, Heidelberg (DE); Ruprecht-Karls-Universität Heidelberg, Heidelberg (DE)

( * ) Notice: Subject to any disclaimer, the term of this patent is extended or adjusted under 35 U.S.C. 154(b) by 0 days.

(21) Appl. No.: 13/509,592

(22) PCT Filed: Nov. 15, 2010

(86) PCT No.: PCT/EP2010/067491
§ 371 (c)(1),
(2), (4) Date: Jul. 31, 2012

(87) PCT Pub. No.: WO2011/058175
PCT Pub. Date: May 19, 2011

(65) Prior Publication Data
US 2012/0294856 A1 Nov. 22, 2012

(30) Foreign Application Priority Data
Nov. 16, 2009 (EP) ..................... 09176099

(51) Int. Cl.
A61K 39/395 (2006.01)
G01N 33/50 (2006.01)
A61K 31/7105 (2006.01)

(52) U.S. Cl.
CPC ........ *G01N 33/5041* (2013.01); *G01N 33/5011* (2013.01); *A61K 31/7105* (2013.01); *G01N 2333/70578* (2013.01)
USPC ..................................................... 424/134.1

(58) Field of Classification Search
CPC ............ A61K 38/1761; A61K 38/177; A61K 38/174; A61K 51/1057
See application file for complete search history.

(56) References Cited

FOREIGN PATENT DOCUMENTS

| WO | WO 99/32619 | 7/1999 |
| WO | WO 2005/038005 A2 | 4/2005 |
| WO | WO 2008/080623 | 7/2008 |
| WO | WO 2008/080623 A2 * | 7/2008 |

OTHER PUBLICATIONS

Kataja et al., Ann Oncol 2009; 20(sup 4): iv10-14.*
Nelson et al., Ann. Intern Med. 2009; 151:727-737.*
Balmana et al. Ann Oncol 2009; 20(supp 4):iv19-20.*
Chen & Xie, Int'l J. Nanomedicine, 2012; 7:3971-80.*
Burnett & Rossi, Chem Biol 2012; 19(1);60-71.*
International Preliminary Report on Patentability cited in related International Patent Application No. PCT/EP2010/067491, mailed May 31, 2012.
International Search Report cited in related International Patent Application No. PCT/EP2010/067491, completed Dec. 15, 2010.
Krammer, "CD95's Deadly Mission in the Immune System," *Nature*, vol. 407, pp. 789-795 (2000).
Kleber et al., "Yes and PI3K Bind CD95 to Signal Invasion of Glioblastoma," *Cancer Cell*, vol. 13, pp. 235-248 (2008).
Pawlik et al., "Evaluating the Impact of Single-Day Multidisciplinary Clinic on the Management of Pancreatic Cancer," *Annals of Surgical Oncology*, vol. 15, No. 8, pp. 2081-2088 (2008).
Liu et al., "Technological Advances in High-Throughput Screening," *Am J. Pharmacogenomics*, vol. 4, No. 4, pp. 263-276 (2004).
Bhindi et al., "DNA Enzymes, Short Interfering RNA, and the Emerging Wave of Small-Molecule Nucleic Acid-Based Gene-Siliencing Strategies," *The Amer. Journ. of Pathology*, vol. 171, No. 4, pp. 1079-1088 (2007).
Hammond et al., "Post-Transcriptional Gene Silencing by Double-Stranded RNA," vol. 2, pp. 110-119 (2001).
Bernstein et al., "Role for a Bidentate Ribonuclease in the Initiation Step of RNA Interference," *Nature*, vol. 409, pp. 363-366, Supplemental pp. 13, (2001).
Elbashir et al., Duplexes of 21-Nucleotide RNAs Mediate RNA Interference in Cultured Mammalian Cells, *Nature*, vol. 411, pp. 494-498 (2001).
Doherty et al., "Ribozyme Strucutres and Mechanisms," Annu. Rev. Biophys. Biomol. Struct., vol. 30, pp. 457-475 (2001).
Citti et al., "Synthetic Hammerhead Ribozymes as Therapeutic Tools to Control Disease Genes," *Current Gene Therapy*, vol. 5, pp. 11-24 (2005).
Achenbach et al., "DNAzymes: From Creation in Vitro to Application in Vivo," *Current Pharmaceutical Biotechnology*, vol. 5, pp. 321-336 (2004).
Kohler et al., "Continuous Cultures of Fused Cells Secreting Antibody of Predefined Specificity," *Nature*, vol. 256, pp. 495-497 (1975).
Galfre et al., "Preparation of Monoclonal Antibodies: Strategies and Procedures," *Methods in Enzymology*, vol. 73, pp. 3-46 (1981).
Mochly-Rosen et al., "A General Procedure for Screening Inhibitory Antibodies: Application for Identifying Anti-Protein Kinase C Antibodies," *Analytical Biochemistry*, vol. 170, pp. 31-37 (1988).

(Continued)

*Primary Examiner* — Sheela J Huff
*Assistant Examiner* — Jessica H Roark
(74) *Attorney, Agent, or Firm* — Foley & Lardner LLP

(57) ABSTRACT

The present invention is concerned with compounds inhibiting CD95 signaling in pancreatic cancer cells. Furthermore, contemplated by the current invention are medicaments comprising such a compound for the prevention and/or treatment of pancreatic cancer as well as the use of such a compound for the manufacture of a medicament for the prevention and/or treatment of pancreatic cancer, the prevention of migration of cancer cells, and/or the prevention and/or treatment of an inflammatory reaction. The present invention also refers to a method for the identification of a compound inhibiting CD95 signaling, as we to a method for the manufacture of a medicament comprising the steps of the method for the identification of a compound inhibiting CD95 signaling and the further step of formulating the inhibiting compound as a medicament.

4 Claims, 8 Drawing Sheets

(56) References Cited

OTHER PUBLICATIONS

Figure 2:
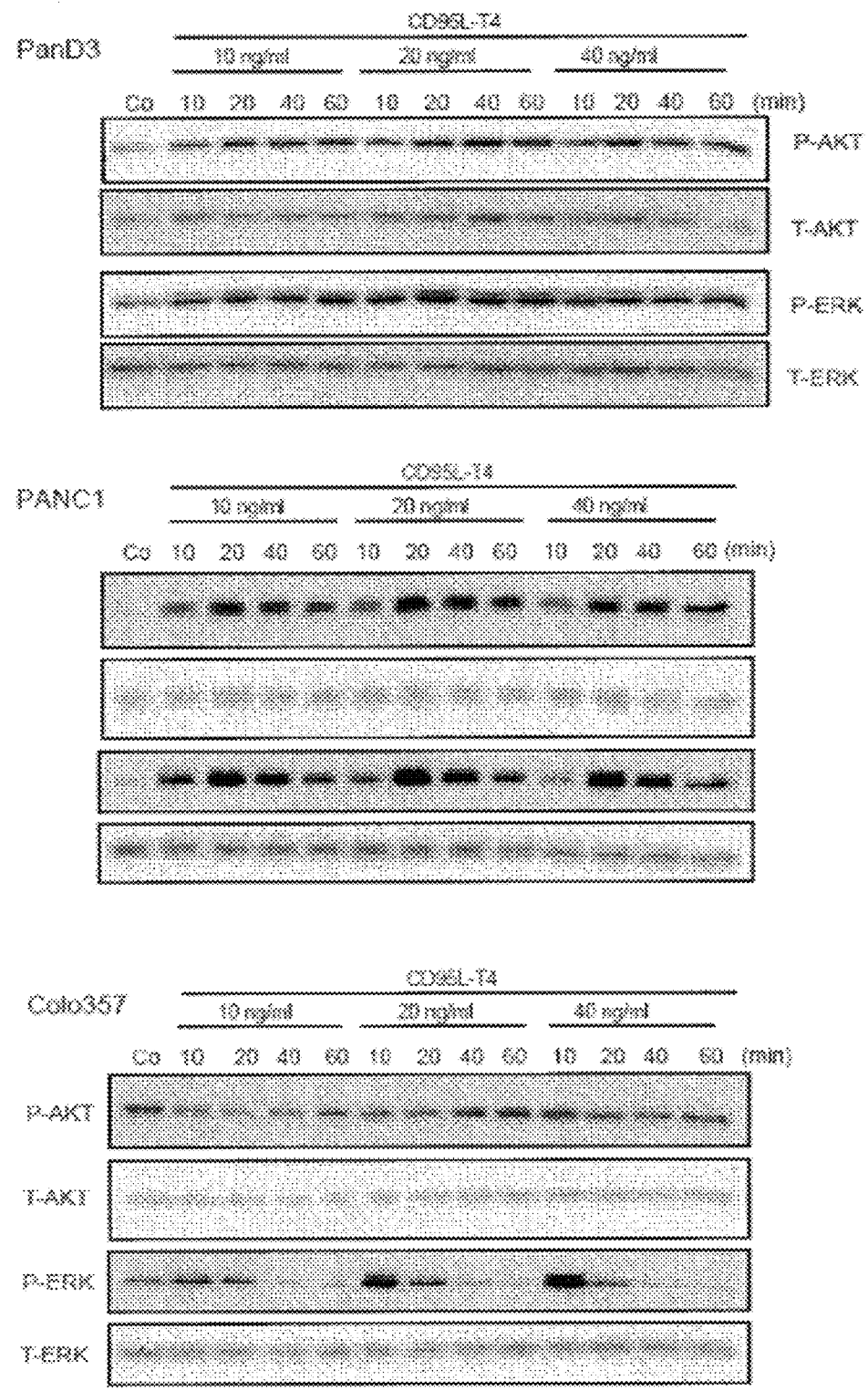

Klevenz et al., "Peptide Aptamers: Exchange of the Thioredoxin-A Scaffold by Alternative Platform Proteins and Its Influence on Target Protein Binding," *MCLS, Cell. Mol. Life Sci.*, vol. 59, pp. 1993-1998 (2002).

Walensky et al., "Activation of Apoptosis in Vivo by a Hydrocarbon-Stapled BH3 Helix," *Science*, vol. 305, pp. 1466-1470 (2004).

Snyder et al., "Cell Penetrating Peptides in Drug Delivery," *Pharmaceutical Research*, vol. 21, No. 3, pp. 389-393 (2004).

Ulrich, "RNA Aptamers: From Basic Science Towards Therapy," *HEP*, vol. 173, pp. 305-326 (2006). 1J.H.R.,.

Ulrich, "DNA and RNA Aptamers as Modulators of Protein Functions," *Medicinal Chem.*, pp. 199-208 (2005).

O'Bryan, "Determining Involvement of Shc Proteins in Signaling Pathways," *Methods in Enzymology*, vol. 333, pp. 3-15 (2001).

Trauzold et al., "CD95 and TRAF2 Promote Invasiveness of Pancreatic Cancer Cells," *The FASEB Journ.*, vol. 19, pp. 620-622 (2005).

Goldberg et al., "New Derivatives of Farnesylthiosalicylic Acid (Salirasib) for Cancer Treatment: Farnesylthiosalicylamide Inhibits Tumor Growth in Nude Mice Models," *J. Med. Chem.*, vol. 52, pp. 197-205 (2009).

Sawai et al., "Activation of Focal Adhesion Kinase Enhances the Adhesion and Invasion of Pancreatic Cancer Cells via Extracellular Signal-Regulated Kinase—1/2 Signaling Pathway Activiation," *Molecular Cancer*, vol. 4, No. 37, pp. 1-12 (2005).

Wen et al., "Nuclear Association of the Cytoplasmic Tail of MUC1 and β-Catenin," *The Journ. of Biological Chemistry*, vol. 278, No. 39, pp. 38029-38039 (2003).

European Search Report issued in related European Patent Application No. 09 17 6099, dated. Apr. 15, 2010.

* cited by examiner

Fig. 1
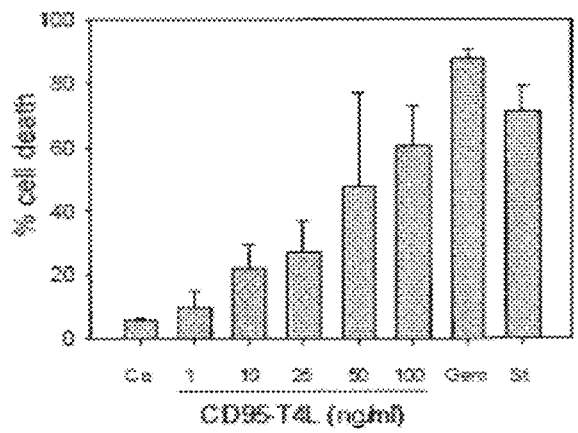
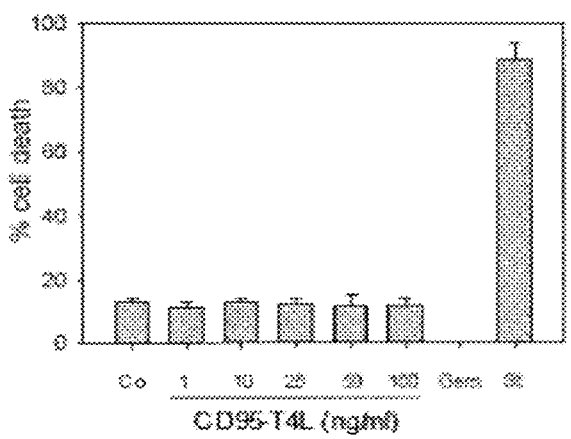
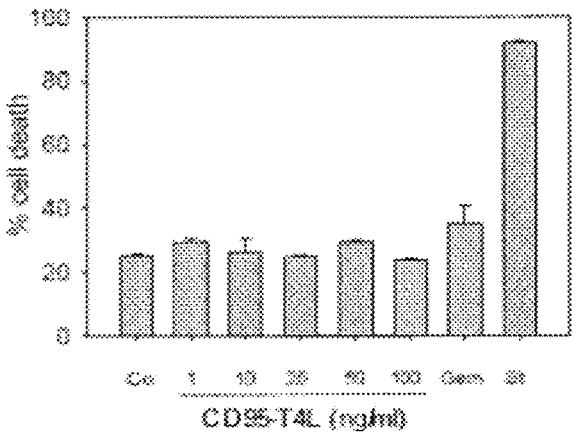

Fig. 3
Colo357
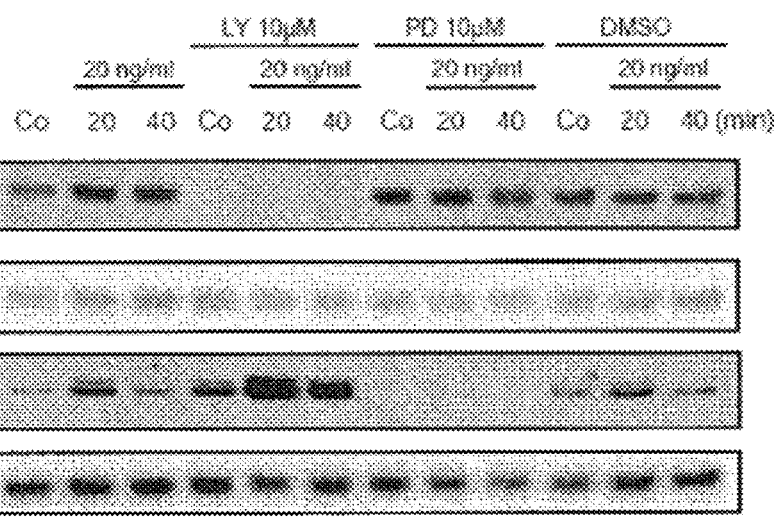
PANC1
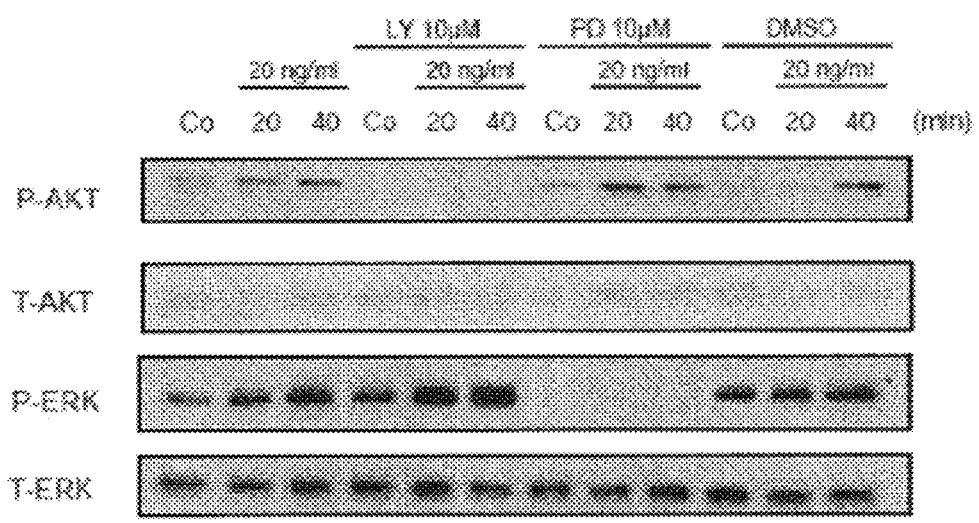
P-AKT
T-AKT
P-ERK
T-ERK

Fig. 5
A)
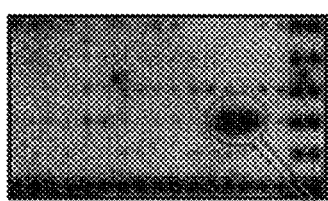
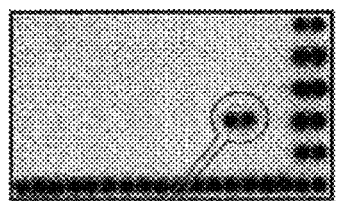
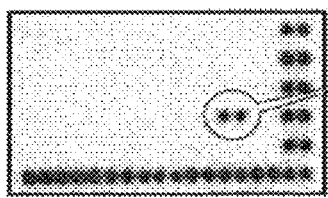
B)
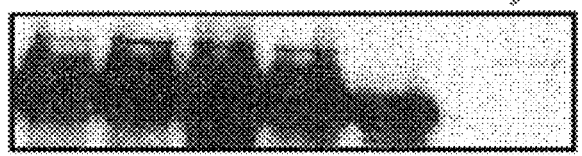

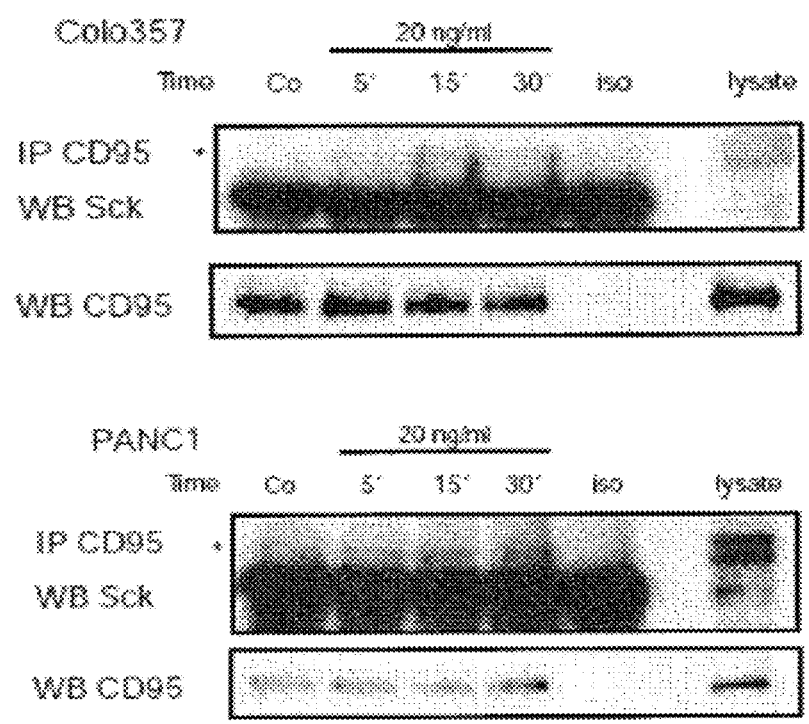

SEQUENCE LISTING

```
<160> NUMBER OF SEQ ID NOS: 24

<210> SEQ ID NO 1
<211> LENGTH: 281
<212> TYPE: PRT
<213> ORGANISM: Homo sapiens

<400> SEQUENCE: 1

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190
```

```
Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
        210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                    245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
                275                 280

<210> SEQ ID NO 2
<211> LENGTH: 335
<212> TYPE: PRT
<213> ORGANISM: Homo sapiens

<400> SEQUENCE: 2

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
                20                  25                  30

Lys Gly Leu Glu Leu Arg Lys Thr Val Thr Thr Val Glu Thr Gln Asn
            35                  40                  45

Leu Glu Gly Leu His His Asp Gly Gln Phe Cys His Lys Pro Cys Pro
50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                    85                  90                  95

Phe Ser Ser Lys Cys Arg Arg Cys Arg Leu Cys Asp Glu Gly His Gly
                100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                    165                 170                 175

Leu Cys Leu Leu Leu Leu Pro Ile Pro Leu Ile Val Trp Val Lys Arg
                180                 185                 190

Lys Glu Val Gln Lys Thr Cys Arg Lys His Arg Lys Glu Asn Gln Gly
            195                 200                 205

Ser His Glu Ser Pro Thr Leu Asn Pro Glu Thr Val Ala Ile Asn Leu
210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                    245                 250                 255

Ala Lys Ile Asp Glu Ile Lys Asn Asp Asn Val Gln Asp Thr Ala Glu
                260                 265                 270

Gln Lys Val Gln Leu Leu Arg Asn Trp His Gln Leu His Gly Lys Lys
```

```
                        275                 280                 285
Glu Ala Tyr Asp Thr Leu Ile Lys Asp Leu Lys Lys Ala Asn Leu Cys
        290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 3
<211> LENGTH: 505
<212> TYPE: PRT
<213> ORGANISM: Homo sapiens

<400> SEQUENCE: 3

Met Gly Leu Val Ser Ser Lys Lys Pro Asp Lys Glu Lys Pro Ile Lys
1               5                   10                  15

Glu Lys Asp Lys Gly Gln Trp Ser Pro Leu Lys Val Ser Ala Gln Asp
            20                  25                  30

Lys Asp Ala Pro Pro Leu Pro Pro Leu Val Val Phe Asn His Leu Thr
        35                  40                  45

Pro Pro Pro Pro Asp Glu His Leu Asp Glu Asp Lys His Phe Val Val
    50                  55                  60

Ala Leu Tyr Asp Tyr Thr Ala Met Asn Asp Arg Asp Leu Gln Met Leu
65                  70                  75                  80

Lys Gly Glu Lys Leu Gln Val Leu Lys Gly Thr Gly Asp Trp Trp Leu
                85                  90                  95

Ala Arg Ser Leu Val Thr Gly Arg Glu Gly Tyr Val Pro Ser Asn Phe
            100                 105                 110

Val Ala Arg Val Glu Ser Leu Glu Met Glu Arg Trp Phe Phe Arg Ser
        115                 120                 125

Gln Gly Arg Lys Glu Ala Glu Arg Gln Leu Leu Ala Pro Ile Asn Lys
    130                 135                 140

Ala Gly Ser Phe Leu Ile Arg Glu Ser Glu Thr Asn Lys Gly Ala Phe
145                 150                 155                 160

Ser Leu Ser Val Lys Asp Val Thr Thr Gln Gly Glu Leu Ile Lys His
                165                 170                 175

Tyr Lys Ile Arg Cys Leu Asp Glu Gly Gly Tyr Tyr Ile Ser Pro Arg
            180                 185                 190

Ile Thr Phe Pro Ser Leu Gln Ala Leu Val Gln His Tyr Ser Lys Lys
        195                 200                 205

Gly Asp Gly Leu Cys Gln Arg Leu Thr Leu Pro Cys Val Arg Pro Ala
    210                 215                 220

Pro Gln Asn Pro Trp Ala Gln Asp Glu Trp Glu Ile Pro Arg Gln Ser
225                 230                 235                 240

Leu Arg Leu Val Arg Lys Leu Gly Ser Gly Gln Phe Gly Glu Val Trp
                245                 250                 255

Met Gly Tyr Tyr Lys Asn Asn Met Lys Val Ala Ile Lys Thr Leu Lys
            260                 265                 270

Glu Gly Thr Met Ser Pro Glu Ala Phe Leu Gly Glu Ala Asn Val Met
        275                 280                 285

Lys Ala Leu Gln His Glu Arg Leu Val Arg Leu Tyr Ala Val Val Thr
    290                 295                 300

Lys Glu Pro Ile Tyr Ile Val Thr Glu Tyr Met Ala Arg Gly Cys Leu
305                 310                 315                 320
```

```
Leu Asp Phe Leu Lys Thr Asp Glu Gly Ser Arg Leu Ser Leu Pro Arg
                325                 330                 335

Leu Ile Asp Met Ser Ala Gln Ile Ala Glu Gly Met Ala Tyr Ile Glu
            340                 345                 350

Arg Met Asn Ser Ile His Arg Asp Leu Arg Ala Ala Asn Ile Leu Val
        355                 360                 365

Ser Glu Ala Leu Cys Cys Lys Ile Ala Asp Phe Gly Leu Ala Arg Ile
370                 375                 380

Ile Asp Ser Glu Tyr Thr Ala Gln Glu Gly Ala Lys Phe Pro Ile Lys
385                 390                 395                 400

Trp Thr Ala Pro Glu Ala Ile His Phe Gly Val Phe Thr Ile Lys Ala
                405                 410                 415

Asp Val Trp Ser Phe Gly Val Leu Leu Met Glu Val Val Thr Tyr Gly
            420                 425                 430

Arg Val Pro Tyr Pro Gly Met Ser Asn Pro Glu Val Ile Arg Asn Leu
        435                 440                 445

Glu Arg Gly Tyr Arg Met Pro Arg Pro Asp Thr Cys Pro Pro Glu Leu
    450                 455                 460

Tyr Arg Gly Val Ile Ala Glu Cys Trp Arg Ser Arg Pro Glu Glu Arg
465                 470                 475                 480

Pro Thr Phe Glu Phe Leu Gln Ser Val Leu Glu Asp Phe Tyr Thr Ala
                485                 490                 495

Thr Glu Arg Gln Tyr Glu Leu Gln Pro
            500                 505

<210> SEQ ID NO 4
<211> LENGTH: 512
<212> TYPE: PRT
<213> ORGANISM: Homo sapiens

<400> SEQUENCE: 4

Met Gly Cys Ile Lys Ser Lys Gly Lys Asp Ser Leu Ser Asp Asp Gly
1               5                   10                  15

Val Asp Leu Lys Thr Gln Pro Val Arg Asn Thr Glu Arg Thr Ile Tyr
            20                  25                  30

Val Arg Asp Pro Thr Ser Asn Lys Gln Gln Arg Pro Val Pro Glu Ser
        35                  40                  45

Gln Leu Leu Pro Gly Gln Arg Phe Gln Thr Lys Asp Pro Glu Glu Gln
    50                  55                  60

Gly Asp Ile Val Val Ala Leu Tyr Pro Tyr Asp Gly Ile His Pro Asp
65                  70                  75                  80

Asp Leu Ser Phe Lys Lys Gly Glu Lys Met Lys Val Leu Glu Glu His
                85                  90                  95

Gly Glu Trp Trp Lys Ala Lys Ser Leu Leu Thr Lys Lys Glu Gly Phe
            100                 105                 110

Ile Pro Ser Asn Tyr Val Ala Lys Leu Asn Thr Leu Glu Thr Glu Glu
        115                 120                 125

Trp Phe Phe Lys Asp Ile Thr Arg Lys Asp Ala Glu Arg Gln Leu Leu
    130                 135                 140

Ala Pro Gly Asn Ser Ala Gly Ala Phe Leu Ile Arg Glu Ser Glu Thr
145                 150                 155                 160

Leu Lys Gly Ser Phe Ser Leu Ser Val Arg Asp Phe Asp Pro Val His
                165                 170                 175

Gly Asp Val Ile Lys His Tyr Lys Ile Arg Ser Leu Asp Asn Gly Gly
            180                 185                 190
```

```
Tyr Tyr Ile Ser Pro Arg Ile Thr Phe Pro Cys Ile Ser Asp Met Ile
        195                 200                 205

Lys His Tyr Gln Lys Gln Ala Asp Gly Leu Cys Arg Arg Leu Glu Lys
        210                 215                 220

Ala Cys Ile Ser Pro Lys Pro Gln Lys Pro Trp Asp Lys Asp Ala Trp
225                 230                 235                 240

Glu Ile Pro Arg Glu Ser Ile Lys Leu Val Lys Arg Leu Gly Ala Gly
                245                 250                 255

Gln Phe Gly Glu Val Trp Met Gly Tyr Tyr Asn Asn Ser Thr Lys Val
                260                 265                 270

Ala Val Lys Thr Leu Lys Pro Gly Thr Met Ser Val Gln Ala Phe Leu
                275                 280                 285

Glu Glu Ala Asn Leu Met Lys Thr Leu Gln His Asp Lys Leu Val Arg
        290                 295                 300

Leu Tyr Ala Val Val Thr Arg Glu Glu Pro Ile Tyr Ile Ile Thr Glu
305                 310                 315                 320

Tyr Met Ala Lys Gly Ser Leu Leu Asp Phe Leu Lys Ser Asp Glu Gly
                325                 330                 335

Gly Lys Val Leu Leu Pro Lys Leu Ile Asp Phe Ser Ala Gln Ile Ala
                340                 345                 350

Glu Gly Met Ala Tyr Ile Glu Arg Lys Asn Tyr Ile His Arg Asp Leu
                355                 360                 365

Arg Ala Ala Asn Val Leu Val Ser Glu Ser Leu Met Cys Lys Ile Ala
        370                 375                 380

Asp Phe Gly Leu Ala Arg Val Ile Glu Asp Asn Glu Tyr Thr Ala Arg
385                 390                 395                 400

Glu Gly Ala Lys Phe Pro Ile Lys Trp Thr Ala Pro Glu Ala Ile Asn
                405                 410                 415

Phe Gly Cys Phe Thr Ile Lys Ser Asp Val Trp Ser Phe Gly Ile Leu
                420                 425                 430

Leu Tyr Glu Ile Val Thr Tyr Gly Lys Ile Pro Tyr Pro Gly Arg Thr
                435                 440                 445

Asn Ala Asp Val Met Thr Ala Leu Ser Gln Gly Tyr Arg Met Pro Arg
        450                 455                 460

Val Glu Asn Cys Pro Asp Glu Leu Tyr Asp Ile Met Lys Met Cys Trp
465                 470                 475                 480

Lys Glu Lys Ala Glu Glu Arg Pro Thr Phe Asp Tyr Leu Gln Ser Val
                485                 490                 495

Leu Asp Asp Phe Tyr Thr Ala Thr Glu Gly Gln Tyr Gln Gln Gln Pro
                500                 505                 510

<210> SEQ ID NO 5
<211> LENGTH: 491
<212> TYPE: PRT
<213> ORGANISM: Homo sapiens

<400> SEQUENCE: 5

Met Gly Cys Ile Lys Ser Lys Gly Lys Asp Ser Leu Ser Asp Gly
1               5                   10                  15

Val Asp Leu Lys Thr Gln Pro Val Pro Glu Ser Gln Leu Leu Pro Gly
                20                  25                  30

Gln Arg Phe Gln Thr Lys Asp Pro Glu Glu Gln Gly Asp Ile Val Val
                35                  40                  45

Ala Leu Tyr Pro Tyr Asp Gly Ile His Pro Asp Asp Leu Ser Phe Lys
```

```
            50                  55                  60
Lys Gly Glu Lys Met Lys Val Leu Glu Glu His Gly Glu Trp Trp Lys
 65                  70                  75                  80

Ala Lys Ser Leu Leu Thr Lys Lys Glu Gly Phe Ile Pro Ser Asn Tyr
                 85                  90                  95

Val Ala Lys Leu Asn Thr Leu Glu Thr Glu Glu Trp Phe Phe Lys Asp
            100                 105                 110

Ile Thr Arg Lys Asp Ala Glu Arg Gln Leu Leu Ala Pro Gly Asn Ser
        115                 120                 125

Ala Gly Ala Phe Leu Ile Arg Glu Ser Glu Thr Leu Lys Gly Ser Phe
    130                 135                 140

Ser Leu Ser Val Arg Asp Phe Asp Pro Val His Gly Asp Val Ile Lys
145                 150                 155                 160

His Tyr Lys Ile Arg Ser Leu Asp Asn Gly Gly Tyr Tyr Ile Ser Pro
                165                 170                 175

Arg Ile Thr Phe Pro Cys Ile Ser Asp Met Ile Lys His Tyr Gln Lys
            180                 185                 190

Gln Ala Asp Gly Leu Cys Arg Arg Leu Glu Lys Ala Cys Ile Ser Pro
        195                 200                 205

Lys Pro Gln Lys Pro Trp Asp Lys Asp Ala Trp Glu Ile Pro Arg Glu
210                 215                 220

Ser Ile Lys Leu Val Lys Arg Leu Gly Ala Gly Gln Phe Gly Glu Val
225                 230                 235                 240

Trp Met Gly Tyr Tyr Asn Asn Ser Thr Lys Val Ala Val Lys Thr Leu
                245                 250                 255

Lys Pro Gly Thr Met Ser Val Gln Ala Phe Leu Glu Glu Ala Asn Leu
            260                 265                 270

Met Lys Thr Leu Gln His Asp Lys Leu Val Arg Leu Tyr Ala Val Val
        275                 280                 285

Thr Arg Glu Glu Pro Ile Tyr Ile Ile Thr Glu Tyr Met Ala Lys Gly
    290                 295                 300

Ser Leu Leu Asp Phe Leu Lys Ser Asp Glu Gly Gly Lys Val Leu Leu
305                 310                 315                 320

Pro Lys Leu Ile Asp Phe Ser Ala Gln Ile Ala Glu Gly Met Ala Tyr
                325                 330                 335

Ile Glu Arg Lys Asn Tyr Ile His Arg Asp Leu Arg Ala Ala Asn Val
            340                 345                 350

Leu Val Ser Glu Ser Leu Met Cys Lys Ile Ala Asp Phe Gly Leu Ala
        355                 360                 365

Arg Val Ile Glu Asp Asn Glu Tyr Thr Ala Arg Glu Gly Ala Lys Phe
    370                 375                 380

Pro Ile Lys Trp Thr Ala Pro Glu Ala Ile Asn Phe Gly Cys Phe Thr
385                 390                 395                 400

Ile Lys Ser Asp Val Trp Ser Phe Gly Ile Leu Leu Tyr Glu Ile Val
                405                 410                 415

Thr Tyr Gly Lys Ile Pro Tyr Pro Gly Arg Thr Asn Ala Asp Val Met
            420                 425                 430

Thr Ala Leu Ser Gln Gly Tyr Arg Met Pro Arg Val Glu Asn Cys Pro
        435                 440                 445

Asp Glu Leu Tyr Asp Ile Met Lys Met Cys Trp Lys Glu Lys Ala Glu
    450                 455                 460

Glu Arg Pro Thr Phe Asp Tyr Leu Gln Ser Val Leu Asp Asp Phe Tyr
465                 470                 475                 480
```

Thr Ala Thr Glu Gly Gln Tyr Gln Gln Gln Pro
            485                 490

<210> SEQ ID NO 6
<211> LENGTH: 526
<212> TYPE: PRT
<213> ORGANISM: Homo sapiens

<400> SEQUENCE: 6

Met Gly Gly Arg Ser Ser Cys Glu Asp Pro Gly Cys Pro Arg Asp Glu
1               5                   10                  15

Glu Arg Ala Pro Arg Met Gly Cys Met Lys Ser Lys Phe Leu Gln Val
            20                  25                  30

Gly Gly Asn Thr Phe Ser Lys Thr Glu Thr Ser Ala Ser Pro His Cys
            35                  40                  45

Pro Val Tyr Val Pro Asp Pro Thr Ser Thr Ile Lys Pro Gly Pro Asn
        50                  55                  60

Ser His Asn Ser Asn Thr Pro Gly Ile Arg Glu Ala Gly Ser Glu Asp
65                  70                  75                  80

Ile Ile Val Val Ala Leu Tyr Asp Tyr Glu Ala Ile His His Glu Asp
                85                  90                  95

Leu Ser Phe Gln Lys Gly Asp Gln Met Val Val Leu Glu Glu Ser Gly
            100                 105                 110

Glu Trp Trp Lys Ala Arg Ser Leu Ala Thr Arg Lys Glu Gly Tyr Ile
            115                 120                 125

Pro Ser Asn Tyr Val Ala Arg Val Asp Ser Leu Glu Thr Glu Glu Trp
        130                 135                 140

Phe Phe Lys Gly Ile Ser Arg Lys Asp Ala Glu Arg Gln Leu Leu Ala
145                 150                 155                 160

Pro Gly Asn Met Leu Gly Ser Phe Met Ile Arg Asp Ser Glu Thr Thr
                165                 170                 175

Lys Gly Ser Tyr Ser Leu Ser Val Arg Asp Tyr Asp Pro Arg Gln Gly
            180                 185                 190

Asp Thr Val Lys His Tyr Lys Ile Arg Thr Leu Asp Asn Gly Gly Phe
        195                 200                 205

Tyr Ile Ser Pro Arg Ser Thr Phe Ser Thr Leu Gln Glu Leu Val Asp
210                 215                 220

His Tyr Lys Lys Gly Asn Asp Gly Leu Cys Gln Lys Leu Ser Val Pro
225                 230                 235                 240

Cys Met Ser Ser Lys Pro Gln Lys Pro Trp Glu Lys Asp Ala Trp Glu
                245                 250                 255

Ile Pro Arg Glu Ser Leu Lys Leu Glu Lys Lys Leu Gly Ala Gly Gln
            260                 265                 270

Phe Gly Glu Val Trp Met Ala Thr Tyr Asn Lys His Thr Lys Val Ala
        275                 280                 285

Val Lys Thr Met Lys Pro Gly Ser Met Ser Val Glu Ala Phe Leu Ala
290                 295                 300

Glu Ala Asn Val Met Lys Thr Leu Gln His Asp Lys Leu Val Lys Leu
305                 310                 315                 320

His Ala Val Val Thr Lys Glu Pro Ile Tyr Ile Ile Thr Glu Phe Met
                325                 330                 335

Ala Lys Gly Ser Leu Leu Asp Phe Leu Lys Ser Asp Glu Gly Ser Lys
            340                 345                 350

Gln Pro Leu Pro Lys Leu Ile Asp Phe Ser Ala Gln Ile Ala Glu Gly

```
            355                 360                 365
Met Ala Phe Ile Glu Gln Arg Asn Tyr Ile His Arg Asp Leu Arg Ala
370                 375                 380

Ala Asn Ile Leu Val Ser Ala Ser Leu Val Cys Lys Ile Ala Asp Phe
385                 390                 395                 400

Gly Leu Ala Arg Val Ile Glu Asp Asn Glu Tyr Thr Ala Arg Glu Gly
                405                 410                 415

Ala Lys Phe Pro Ile Lys Trp Thr Ala Pro Glu Ala Ile Asn Phe Gly
            420                 425                 430

Ser Phe Thr Ile Lys Ser Asp Val Trp Ser Phe Gly Ile Leu Leu Met
        435                 440                 445

Glu Ile Val Thr Tyr Gly Arg Ile Pro Tyr Pro Gly Met Ser Asn Pro
450                 455                 460

Glu Val Ile Arg Ala Leu Glu Arg Gly Tyr Arg Met Pro Arg Pro Glu
465                 470                 475                 480

Asn Cys Pro Glu Glu Leu Tyr Asn Ile Met Met Arg Cys Trp Lys Asn
                485                 490                 495

Arg Pro Glu Glu Arg Pro Thr Phe Glu Tyr Ile Gln Ser Val Leu Asp
            500                 505                 510

Asp Phe Tyr Thr Ala Thr Glu Ser Gln Tyr Gln Gln Pro
        515                 520                 525

<210> SEQ ID NO 7
<211> LENGTH: 536
<212> TYPE: PRT
<213> ORGANISM: Homo sapiens

<400> SEQUENCE: 7

Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Gly Ala Phe
            20                  25                  30

Pro Ala Ser Gln Thr Pro Ser Lys Pro Ala Ser Ala Asp Gly His Arg
        35                  40                  45

Gly Pro Ser Ala Ala Phe Ala Pro Ala Ala Ala Glu Pro Lys Leu Phe
    50                  55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
        115                 120                 125

Thr Gly Gln Thr Gly Tyr Ile Pro Ser Asn Tyr Val Ala Pro Ser Asp
    130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
        195                 200                 205
```

Lys Leu Asp Ser Gly Gly Phe Tyr Ile Thr Ser Arg Thr Gln Phe Asn
210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
                260                 265                 270

Glu Val Lys Leu Gly Gln Gly Cys Phe Gly Glu Val Trp Met Gly Thr
            275                 280                 285

Trp Asn Gly Thr Thr Arg Val Ala Ile Lys Thr Leu Lys Pro Gly Thr
290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
                340                 345                 350

Leu Lys Gly Glu Thr Gly Lys Tyr Leu Arg Leu Pro Gln Leu Val Asp
            355                 360                 365

Met Ala Ala Gln Ile Ala Ser Gly Met Ala Tyr Val Glu Arg Met Asn
370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
                420                 425                 430

Ala Pro Glu Ala Ala Leu Tyr Gly Arg Phe Thr Ile Lys Ser Asp Val
            435                 440                 445

Trp Ser Phe Gly Ile Leu Leu Thr Glu Leu Thr Thr Lys Gly Arg Val
450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
                500                 505                 510

Glu Tyr Leu Gln Ala Phe Leu Glu Asp Tyr Phe Thr Ser Thr Glu Pro
            515                 520                 525

Gln Tyr Gln Pro Gly Glu Asn Leu
530                 535

<210> SEQ ID NO 8
<211> LENGTH: 529
<212> TYPE: PRT
<213> ORGANISM: Homo sapiens

<400> SEQUENCE: 8

Met Gly Cys Val Phe Cys Lys Lys Leu Glu Pro Val Ala Thr Ala Lys
1               5                   10                  15

Glu Asp Ala Gly Leu Glu Gly Asp Phe Arg Ser Tyr Gly Ala Ala Asp
                20                  25                  30

His Tyr Gly Pro Asp Pro Thr Lys Ala Arg Pro Ala Ser Ser Phe Ala
            35                  40                  45

-continued

His Ile Pro Asn Tyr Ser Asn Phe Ser Ser Gln Ala Ile Asn Pro Gly
                50                  55                  60

Phe Leu Asp Ser Gly Thr Ile Arg Gly Val Ser Gly Ile Gly Val Thr
 65                  70                  75                  80

Leu Phe Ile Ala Leu Tyr Asp Tyr Glu Ala Arg Thr Glu Asp Asp Leu
                 85                  90                  95

Thr Phe Thr Lys Gly Glu Lys Phe His Ile Leu Asn Asn Thr Glu Gly
                100                 105                 110

Asp Trp Trp Glu Ala Arg Ser Leu Ser Ser Gly Lys Thr Gly Cys Ile
                115                 120                 125

Pro Ser Asn Tyr Val Ala Pro Val Asp Ser Ile Gln Ala Glu Glu Trp
                130                 135                 140

Tyr Phe Gly Lys Ile Gly Arg Lys Asp Ala Glu Arg Gln Leu Leu Ser
145                 150                 155                 160

Pro Gly Asn Pro Gln Gly Ala Phe Leu Ile Arg Glu Ser Glu Thr Thr
                165                 170                 175

Lys Gly Ala Tyr Ser Leu Ser Ile Arg Asp Trp Asp Gln Thr Arg Gly
                180                 185                 190

Asp His Val Lys His Tyr Lys Ile Arg Lys Leu Asp Met Gly Gly Tyr
                195                 200                 205

Tyr Ile Thr Thr Arg Val Gln Phe Asn Ser Val Gln Glu Leu Val Gln
210                 215                 220

His Tyr Met Glu Val Asn Asp Gly Leu Cys Asn Leu Leu Ile Ala Pro
225                 230                 235                 240

Cys Thr Ile Met Lys Pro Gln Thr Leu Gly Leu Ala Lys Asp Ala Trp
                245                 250                 255

Glu Ile Ser Arg Ser Ser Ile Thr Leu Glu Arg Arg Leu Gly Thr Gly
                260                 265                 270

Cys Phe Gly Asp Val Trp Leu Gly Thr Trp Asn Gly Ser Thr Lys Val
                275                 280                 285

Ala Val Lys Thr Leu Lys Pro Gly Thr Met Ser Pro Lys Ala Phe Leu
                290                 295                 300

Glu Glu Ala Gln Val Met Lys Leu Leu Arg His Asp Lys Leu Val Gln
305                 310                 315                 320

Leu Tyr Ala Val Val Ser Glu Glu Pro Ile Tyr Ile Val Thr Glu Phe
                325                 330                 335

Met Cys His Gly Ser Leu Leu Asp Phe Leu Lys Asn Pro Glu Gly Gln
                340                 345                 350

Asp Leu Arg Leu Pro Gln Leu Val Asp Met Ala Ala Gln Val Ala Glu
                355                 360                 365

Gly Met Ala Tyr Met Glu Arg Met Asn Tyr Ile His Arg Asp Leu Arg
                370                 375                 380

Ala Ala Asn Ile Leu Val Gly Glu Arg Leu Ala Cys Lys Ile Ala Asp
385                 390                 395                 400

Phe Gly Leu Ala Arg Leu Ile Lys Asp Asp Glu Tyr Asn Pro Cys Gln
                405                 410                 415

Gly Ser Lys Phe Pro Ile Lys Trp Thr Ala Pro Glu Ala Ala Leu Phe
                420                 425                 430

Gly Arg Phe Thr Ile Lys Ser Asp Val Trp Ser Phe Gly Ile Leu Leu
                435                 440                 445

Thr Glu Leu Ile Thr Lys Gly Arg Ile Pro Tyr Pro Gly Met Asn Lys
450                 455                 460

Arg Glu Val Leu Glu Gln Val Glu Gln Gly Tyr His Met Pro Cys Pro
465                 470                 475                 480

Pro Gly Cys Pro Ala Ser Leu Tyr Glu Ala Met Glu Gln Thr Trp Arg
            485                 490                 495

Leu Asp Pro Glu Glu Arg Pro Thr Phe Glu Tyr Leu Gln Ser Phe Leu
        500                 505                 510

Glu Asp Tyr Phe Thr Ser Ala Glu Pro Gln Tyr Gln Pro Gly Asp Gln
            515                 520                 525

Thr

<210> SEQ ID NO 9
<211> LENGTH: 509
<212> TYPE: PRT
<213> ORGANISM: Homo sapiens

<400> SEQUENCE: 9

Met Gly Cys Gly Cys Ser Ser His Pro Glu Asp Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
        35                  40                  45

Val Thr Tyr Glu Gly Ser Asn Pro Pro Ala Ser Pro Leu Gln Asp Asn
50                  55                  60

Leu Val Ile Ala Leu His Ser Tyr Glu Pro Ser His Asp Gly Asp Leu
65                  70                  75                  80

Gly Phe Glu Lys Gly Glu Gln Leu Arg Ile Leu Glu Gln Ser Gly Glu
                85                  90                  95

Trp Trp Lys Ala Gln Ser Leu Thr Thr Gly Gln Glu Gly Phe Ile Pro
            100                 105                 110

Phe Asn Phe Val Ala Lys Ala Asn Ser Leu Glu Pro Glu Pro Trp Phe
        115                 120                 125

Phe Lys Asn Leu Ser Arg Lys Asp Ala Glu Arg Gln Leu Leu Ala Pro
130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
            180                 185                 190

Ile Ser Pro Arg Ile Thr Phe Pro Gly Leu His Glu Leu Val Arg His
        195                 200                 205

Tyr Thr Asn Ala Ser Asp Gly Leu Cys Thr Arg Leu Ser Arg Pro Cys
210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
            260                 265                 270

Lys Ser Leu Lys Gln Gly Ser Met Ser Pro Asp Ala Phe Leu Ala Glu
        275                 280                 285

Ala Asn Leu Met Lys Gln Leu Gln His Gln Arg Leu Val Arg Leu Tyr
290                 295                 300

```
Ala Val Val Thr Gln Glu Pro Ile Tyr Ile Thr Glu Tyr Met Glu
305                 310                 315                 320

Asn Gly Ser Leu Val Asp Phe Leu Lys Thr Pro Ser Gly Ile Lys Leu
                325                 330                 335

Thr Ile Asn Lys Leu Leu Asp Met Ala Ala Gln Ile Ala Glu Gly Met
            340                 345                 350

Ala Phe Ile Glu Glu Arg Asn Tyr Ile His Arg Asp Leu Arg Ala Ala
        355                 360                 365

Asn Ile Leu Val Ser Asp Thr Leu Ser Cys Lys Ile Ala Asp Phe Gly
    370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
                405                 410                 415

Phe Thr Ile Lys Ser Asp Val Trp Ser Phe Gly Ile Leu Leu Thr Glu
            420                 425                 430

Ile Val Thr His Gly Arg Ile Pro Tyr Pro Gly Met Thr Asn Pro Glu
        435                 440                 445

Val Ile Gln Asn Leu Glu Arg Gly Tyr Arg Met Val Arg Pro Asp Asn
    450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln Pro
                500                 505

<210> SEQ ID NO 10
<211> LENGTH: 482
<212> TYPE: PRT
<213> ORGANISM: Homo sapiens

<400> SEQUENCE: 10

Met Gly Cys Val Gln Cys Lys Asp Lys Glu Ala Thr Lys Leu Thr Glu
1               5                   10                  15

Glu Arg Asp Gly Ser Leu Asn Gln Ser Ser Gly Tyr Arg Tyr Gly Thr
                20                  25                  30

Asp Pro Thr Pro Gln His Tyr Pro Ser Phe Gly Val Thr Ser Ile Pro
            35                  40                  45

Asn Tyr Asn Asn Phe His Ala Ala Gly Gly Gln Gly Leu Thr Val Phe
        50                  55                  60

Gly Gly Val Asn Ser Ser Ser His Thr Gly Thr Leu Arg Thr Arg Gly
65                  70                  75                  80

Gly Thr Gly Val Thr Leu Phe Val Ala Leu Tyr Asp Tyr Glu Ala Arg
                85                  90                  95

Thr Glu Asp Asp Leu Ser Phe His Lys Gly Glu Lys Phe Gln Ile Leu
            100                 105                 110

Asn Ser Ser Glu Gly Asp Trp Trp Glu Ala Arg Ser Leu Thr Thr Gly
        115                 120                 125

Glu Thr Gly Tyr Ile Pro Ser Asn Tyr Val Ala Pro Val Asp Ser Ile
    130                 135                 140

Gln Ala Glu Glu Trp Tyr Phe Gly Lys Leu Gly Arg Lys Asp Ala Glu
145                 150                 155                 160

Arg Gln Leu Leu Ser Phe Gly Asn Pro Arg Gly Thr Phe Leu Ile Arg
                165                 170                 175
```

```
Glu Ser Glu Thr Thr Lys Gly Ala Tyr Ser Leu Ser Ile Arg Asp Trp
            180                 185                 190

Asp Asp Met Lys Gly Asp His Val Lys His Tyr Lys Ile Arg Lys Leu
        195                 200                 205

Asp Asn Gly Gly Tyr Tyr Ile Thr Thr Arg Ala Gln Phe Glu Thr Leu
    210                 215                 220

Gln Gln Leu Val Gln His Tyr Ser Gly Thr Trp Asn Gly Asn Thr Lys
225                 230                 235                 240

Val Ala Ile Lys Thr Leu Lys Pro Gly Thr Met Ser Pro Glu Ser Phe
                245                 250                 255

Leu Glu Glu Ala Gln Ile Met Lys Lys Leu Lys His Asp Lys Leu Val
            260                 265                 270

Gln Leu Tyr Ala Val Val Ser Glu Glu Pro Ile Tyr Ile Val Thr Glu
        275                 280                 285

Tyr Met Asn Lys Gly Ser Leu Leu Asp Phe Leu Lys Asp Gly Glu Gly
    290                 295                 300

Arg Ala Leu Lys Leu Pro Asn Leu Val Asp Met Ala Ala Gln Val Ala
305                 310                 315                 320

Ala Gly Met Ala Tyr Ile Glu Arg Met Asn Tyr Ile His Arg Asp Leu
                325                 330                 335

Arg Ser Ala Asn Ile Leu Val Gly Asn Gly Leu Ile Cys Lys Ile Ala
            340                 345                 350

Asp Phe Gly Leu Ala Arg Leu Ile Glu Asp Asn Glu Tyr Thr Ala Arg
        355                 360                 365

Gln Gly Ala Lys Phe Pro Ile Lys Trp Thr Ala Pro Glu Ala Ala Leu
    370                 375                 380

Tyr Gly Arg Phe Thr Ile Lys Ser Asp Val Trp Ser Phe Gly Ile Leu
385                 390                 395                 400

Leu Thr Glu Leu Val Thr Lys Gly Arg Val Pro Tyr Pro Gly Met Asn
                405                 410                 415

Asn Arg Glu Val Leu Glu Gln Val Glu Arg Gly Tyr Arg Met Pro Cys
            420                 425                 430

Pro Gln Asp Cys Pro Ile Ser Leu His Glu Leu Met Ile His Cys Trp
        435                 440                 445

Lys Lys Asp Pro Glu Glu Arg Pro Thr Phe Glu Tyr Leu Gln Ser Phe
    450                 455                 460

Leu Glu Asp Tyr Phe Thr Ala Thr Glu Pro Gln Tyr Gln Pro Gly Glu
465                 470                 475                 480

Asn Leu

<210> SEQ ID NO 11
<211> LENGTH: 543
<212> TYPE: PRT
<213> ORGANISM: Homo sapiens

<400> SEQUENCE: 11

Met Gly Cys Ile Lys Ser Lys Glu Asn Lys Ser Pro Ala Ile Lys Tyr
1               5                   10                  15

Arg Pro Glu Asn Thr Pro Glu Pro Val Ser Thr Ser Val Ser His Tyr
            20                  25                  30

Gly Ala Glu Pro Thr Thr Val Ser Pro Cys Pro Ser Ser Ser Ala Lys
        35                  40                  45

Gly Thr Ala Val Asn Phe Ser Ser Leu Ser Met Thr Pro Phe Gly Gly
    50                  55                  60
```

-continued

```
Ser Ser Gly Val Thr Pro Phe Gly Gly Ala Ser Ser Phe Ser Val
 65                  70                  75                  80

Val Pro Ser Ser Tyr Pro Ala Gly Leu Thr Gly Gly Val Thr Ile Phe
                 85                  90                  95

Val Ala Leu Tyr Asp Tyr Glu Ala Arg Thr Thr Glu Asp Leu Ser Phe
            100                 105                 110

Lys Lys Gly Glu Arg Phe Gln Ile Ile Asn Asn Thr Glu Gly Asp Trp
        115                 120                 125

Trp Glu Ala Arg Ser Ile Ala Thr Gly Lys Asn Gly Tyr Ile Pro Ser
    130                 135                 140

Asn Tyr Val Ala Pro Ala Asp Ser Ile Gln Ala Glu Glu Trp Tyr Phe
145                 150                 155                 160

Gly Lys Met Gly Arg Lys Asp Ala Glu Arg Leu Leu Leu Asn Pro Gly
                165                 170                 175

Asn Gln Arg Gly Ile Phe Leu Val Arg Glu Ser Glu Thr Thr Lys Gly
            180                 185                 190

Ala Tyr Ser Leu Ser Ile Arg Asp Trp Asp Glu Ile Arg Gly Asp Asn
        195                 200                 205

Val Lys His Tyr Lys Ile Arg Lys Leu Asp Asn Gly Gly Tyr Tyr Ile
    210                 215                 220

Thr Thr Arg Ala Gln Phe Asp Thr Leu Gln Lys Leu Val Lys His Tyr
225                 230                 235                 240

Thr Glu His Ala Asp Gly Leu Cys His Lys Leu Thr Thr Val Cys Pro
                245                 250                 255

Thr Val Lys Pro Gln Thr Gln Gly Leu Ala Lys Asp Ala Trp Glu Ile
            260                 265                 270

Pro Arg Glu Ser Leu Arg Leu Glu Val Lys Leu Gly Gln Gly Cys Phe
        275                 280                 285

Gly Glu Val Trp Met Gly Thr Trp Asn Gly Thr Thr Lys Val Ala Ile
    290                 295                 300

Lys Thr Leu Lys Pro Gly Thr Met Met Pro Glu Ala Phe Leu Gln Glu
305                 310                 315                 320

Ala Gln Ile Met Lys Lys Leu Arg His Asp Lys Leu Val Pro Leu Tyr
                325                 330                 335

Ala Val Val Ser Glu Glu Pro Ile Tyr Ile Val Thr Glu Phe Met Ser
            340                 345                 350

Lys Gly Ser Leu Leu Asp Phe Leu Lys Glu Gly Asp Gly Lys Tyr Leu
        355                 360                 365

Lys Leu Pro Gln Leu Val Asp Met Ala Ala Gln Ile Ala Asp Gly Met
    370                 375                 380

Ala Tyr Ile Glu Arg Met Asn Tyr Ile His Arg Asp Leu Arg Ala Ala
385                 390                 395                 400

Asn Ile Leu Val Gly Glu Asn Leu Val Cys Lys Ile Ala Asp Phe Gly
                405                 410                 415

Leu Ala Arg Leu Ile Glu Asp Asn Glu Tyr Thr Ala Arg Gln Gly Ala
            420                 425                 430

Lys Phe Pro Ile Lys Trp Thr Ala Pro Glu Ala Ala Leu Tyr Gly Arg
        435                 440                 445

Phe Thr Ile Lys Ser Asp Val Trp Ser Phe Gly Ile Leu Gln Thr Glu
    450                 455                 460

Leu Val Thr Lys Gly Arg Val Pro Tyr Pro Gly Met Val Asn Arg Glu
465                 470                 475                 480
```

```
Val Leu Glu Gln Val Glu Arg Gly Tyr Arg Met Pro Cys Pro Gln Gly
                485                 490                 495

Cys Pro Glu Ser Leu His Glu Leu Met Asn Leu Cys Trp Lys Lys Asp
            500                 505                 510

Pro Asp Glu Arg Pro Thr Phe Glu Tyr Ile Gln Ser Phe Leu Glu Asp
            515                 520                 525

Tyr Phe Thr Ala Thr Glu Pro Gln Tyr Gln Pro Gly Glu Asn Leu
            530                 535                 540
```

<210> SEQ ID NO 12
<211> LENGTH: 217
<212> TYPE: PRT
<213> ORGANISM: Homo sapiens

<400> SEQUENCE: 12

```
Met Glu Ala Ile Ala Lys Tyr Asp Phe Lys Ala Thr Ala Asp Asp Glu
1               5                   10                  15

Leu Ser Phe Lys Arg Gly Asp Ile Leu Lys Val Leu Asn Glu Glu Cys
            20                  25                  30

Asp Gln Asn Trp Tyr Lys Ala Glu Leu Asn Gly Lys Asp Gly Phe Ile
            35                  40                  45

Pro Lys Asn Tyr Ile Glu Met Lys Pro His Pro Trp Phe Phe Gly Lys
        50                  55                  60

Ile Pro Arg Ala Lys Ala Glu Glu Met Leu Ser Lys Gln Arg His Asp
65                  70                  75                  80

Gly Ala Phe Leu Ile Arg Glu Ser Glu Ser Ala Pro Gly Asp Phe Ser
                85                  90                  95

Leu Ser Val Lys Phe Gly Asn Asp Val Gln His Phe Lys Val Leu Arg
            100                 105                 110

Asp Gly Ala Gly Lys Tyr Phe Leu Trp Val Val Lys Phe Asn Ser Leu
            115                 120                 125

Asn Glu Leu Val Asp Tyr His Arg Ser Thr Ser Val Ser Arg Asn Gln
        130                 135                 140

Gln Ile Phe Leu Arg Asp Ile Glu Gln Val Pro Gln Gln Pro Thr Tyr
145                 150                 155                 160

Val Gln Ala Leu Phe Asp Phe Asp Pro Gln Glu Asp Gly Glu Leu Gly
                165                 170                 175

Phe Arg Arg Gly Asp Phe Ile His Val Met Asp Asn Ser Asp Pro Asn
            180                 185                 190

Trp Trp Lys Gly Ala Cys His Gly Gln Thr Gly Met Phe Pro Arg Asn
            195                 200                 205

Tyr Val Thr Pro Val Asn Arg Asn Val
        210                 215
```

<210> SEQ ID NO 13
<211> LENGTH: 176
<212> TYPE: PRT
<213> ORGANISM: Homo sapiens

<400> SEQUENCE: 13

```
Met Glu Ala Ile Ala Lys Tyr Asp Phe Lys Ala Thr Ala Asp Asp Glu
1               5                   10                  15

Leu Ser Phe Lys Arg Gly Asp Ile Leu Lys Val Leu Asn Glu Glu Cys
            20                  25                  30

Asp Gln Asn Trp Tyr Lys Ala Glu Leu Asn Gly Lys Asp Gly Phe Ile
            35                  40                  45
```

```
Pro Lys Asn Tyr Ile Glu Met Lys Pro His Pro Phe Gly Asn Asp Val
    50                  55                  60

Gln His Phe Lys Val Leu Arg Asp Gly Ala Gly Lys Tyr Phe Leu Trp
65                  70                  75                  80

Val Val Lys Phe Asn Ser Leu Asn Glu Leu Val Asp Tyr His Arg Ser
                85                  90                  95

Thr Ser Val Ser Arg Asn Gln Gln Ile Phe Leu Arg Asp Ile Glu Gln
            100                 105                 110

Val Pro Gln Gln Pro Thr Tyr Val Gln Ala Leu Phe Asp Phe Asp Pro
        115                 120                 125

Gln Glu Asp Gly Glu Leu Gly Phe Arg Arg Gly Asp Phe Ile His Val
130                 135                 140

Met Asp Asn Ser Asp Pro Asn Trp Trp Lys Gly Ala Cys His Gly Gln
145                 150                 155                 160

Thr Gly Met Phe Pro Arg Asn Tyr Val Thr Pro Val Asn Arg Asn Val
                165                 170                 175

<210> SEQ ID NO 14
<211> LENGTH: 1333
<212> TYPE: PRT
<213> ORGANISM: Homo sapiens

<400> SEQUENCE: 14

Met Gln Ala Gln Gln Leu Pro Tyr Glu Phe Phe Ser Glu Glu Asn Ala
1               5                   10                  15

Pro Lys Trp Arg Gly Leu Leu Val Pro Ala Leu Lys Lys Val Gln Gly
            20                  25                  30

Gln Val His Pro Thr Leu Glu Ser Asn Asp Asp Ala Leu Gln Tyr Val
        35                  40                  45

Glu Glu Leu Ile Leu Gln Leu Leu Asn Met Leu Cys Gln Ala Gln Pro
    50                  55                  60

Arg Ser Ala Ser Asp Val Glu Glu Arg Val Gln Lys Ser Phe Pro His
65                  70                  75                  80

Pro Ile Asp Lys Trp Ala Ile Ala Asp Ala Gln Ser Ala Ile Glu Lys
                85                  90                  95

Arg Lys Arg Arg Asn Pro Leu Ser Leu Pro Val Glu Lys Ile His Pro
            100                 105                 110

Leu Leu Lys Glu Val Leu Gly Tyr Lys Ile Asp His Gln Val Ser Val
        115                 120                 125

Tyr Ile Val Ala Val Leu Glu Tyr Ile Ser Ala Asp Ile Leu Lys Leu
130                 135                 140

Val Gly Asn Tyr Val Arg Asn Ile Arg His Tyr Glu Ile Thr Lys Gln
145                 150                 155                 160

Asp Ile Lys Val Ala Met Cys Ala Asp Lys Val Leu Met Asp Met Phe
                165                 170                 175

His Gln Asp Val Glu Asp Ile Asn Ile Leu Ser Leu Thr Asp Glu Glu
            180                 185                 190

Pro Ser Thr Ser Gly Glu Gln Thr Tyr Tyr Asp Leu Val Lys Ala Phe
        195                 200                 205

Met Ala Glu Ile Arg Gln Tyr Ile Arg Glu Leu Asn Leu Ile Ile Lys
210                 215                 220

Val Phe Arg Glu Pro Phe Val Ser Asn Ser Lys Leu Phe Ser Ala Asn
225                 230                 235                 240

Asp Val Glu Asn Ile Phe Ser Arg Ile Val Asp Ile His Glu Leu Ser
                245                 250                 255
```

```
Val Lys Leu Leu Gly His Ile Glu Asp Thr Val Met Thr Asp Glu
            260                 265                 270

Gly Ser Pro His Pro Leu Val Gly Ser Cys Phe Glu Asp Leu Ala Glu
        275                 280                 285

Glu Leu Ala Phe Asp Pro Tyr Glu Ser Tyr Ala Arg Asp Ile Leu Arg
    290                 295                 300

Pro Gly Phe His Asp Arg Phe Leu Ser Gln Leu Ser Lys Pro Gly Ala
305                 310                 315                 320

Ala Leu Tyr Leu Gln Ser Ile Gly Glu Gly Phe Lys Glu Ala Val Gln
            325                 330                 335

Tyr Val Leu Pro Arg Leu Leu Leu Ala Pro Val Tyr His Cys Leu His
            340                 345                 350

Tyr Phe Glu Leu Leu Lys Gln Leu Glu Lys Ser Glu Asp Gln Glu
            355                 360                 365

Asp Lys Glu Cys Leu Lys Gln Ala Ile Thr Ala Leu Leu Asn Val Gln
    370                 375                 380

Ser Gly Met Glu Lys Ile Cys Ser Lys Ser Leu Ala Lys Arg Arg Leu
385                 390                 395                 400

Ser Glu Ser Ala Cys Arg Phe Tyr Ser Gln Gln Met Lys Gly Lys Gln
                405                 410                 415

Leu Ala Ile Lys Lys Met Asn Glu Ile Gln Lys Asn Ile Asp Gly Trp
            420                 425                 430

Glu Gly Lys Asp Ile Gly Gln Cys Cys Asn Glu Phe Ile Met Glu Gly
        435                 440                 445

Thr Leu Thr Arg Val Gly Ala Lys His Glu Arg His Ile Phe Leu Phe
    450                 455                 460

Asp Gly Leu Met Ile Cys Cys Lys Ser Asn His Gly Gln Pro Arg Leu
465                 470                 475                 480

Pro Gly Ala Ser Asn Ala Glu Tyr Arg Leu Lys Glu Lys Phe Phe Met
            485                 490                 495

Arg Lys Val Gln Ile Asn Asp Lys Asp Asp Thr Asn Glu Tyr Lys His
            500                 505                 510

Ala Phe Glu Ile Ile Leu Lys Asp Glu Asn Ser Val Ile Phe Ser Ala
        515                 520                 525

Lys Ser Ala Glu Glu Lys Asn Asn Trp Met Ala Ala Leu Ile Ser Leu
530                 535                 540

Gln Tyr Arg Ser Thr Leu Glu Arg Met Leu Asp Val Thr Met Leu Gln
545                 550                 555                 560

Glu Glu Lys Glu Glu Gln Met Arg Leu Pro Ser Ala Asp Val Tyr Arg
                565                 570                 575

Phe Ala Glu Pro Asp Ser Glu Glu Asn Ile Ile Phe Glu Glu Asn Met
            580                 585                 590

Gln Pro Lys Ala Gly Ile Pro Ile Ile Lys Ala Gly Thr Val Ile Lys
        595                 600                 605

Leu Ile Glu Arg Leu Thr Tyr His Met Tyr Ala Asp Pro Asn Phe Val
    610                 615                 620

Arg Thr Phe Leu Thr Thr Tyr Arg Ser Phe Cys Lys Pro Gln Glu Leu
625                 630                 635                 640

Leu Ser Leu Ile Ile Glu Arg Phe Glu Ile Pro Glu Pro Glu Pro Thr
            645                 650                 655

Glu Ala Asp Arg Ile Ala Ile Glu Asn Gly Asp Gln Pro Leu Ser Ala
            660                 665                 670
```

-continued

```
Glu Leu Lys Arg Phe Arg Lys Glu Tyr Ile Gln Pro Val Gln Leu Arg
            675                 680                 685

Val Leu Asn Val Cys Arg His Trp Val Glu His His Phe Tyr Asp Phe
        690                 695                 700

Glu Arg Asp Ala Tyr Leu Leu Gln Arg Met Glu Glu Phe Ile Gly Thr
705                 710                 715                 720

Val Arg Gly Lys Ala Met Lys Lys Trp Val Glu Ser Ile Thr Lys Ile
                725                 730                 735

Ile Gln Arg Lys Lys Ile Ala Arg Asp Asn Gly Pro Gly His Asn Ile
            740                 745                 750

Thr Phe Gln Ser Ser Pro Pro Thr Val Glu Trp His Ile Ser Arg Pro
        755                 760                 765

Gly His Ile Glu Thr Phe Asp Leu Leu Thr Leu His Pro Ile Glu Ile
    770                 775                 780

Ala Arg Gln Leu Thr Leu Leu Glu Ser Asp Leu Tyr Arg Ala Val Gln
785                 790                 795                 800

Pro Ser Glu Leu Val Gly Ser Val Trp Thr Lys Glu Asp Lys Glu Ile
                805                 810                 815

Asn Ser Pro Asn Leu Leu Lys Met Ile Arg His Thr Thr Asn Leu Thr
            820                 825                 830

Leu Trp Phe Glu Lys Cys Ile Val Glu Thr Glu Asn Leu Glu Glu Arg
        835                 840                 845

Val Ala Val Val Ser Arg Ile Ile Glu Ile Leu Gln Val Phe Gln Glu
    850                 855                 860

Leu Asn Asn Phe Asn Gly Val Leu Glu Val Val Ser Ala Met Asn Ser
865                 870                 875                 880

Ser Pro Val Tyr Arg Leu Asp His Thr Phe Glu Gln Ile Pro Ser Arg
                885                 890                 895

Gln Lys Lys Ile Leu Glu Glu Ala His Glu Leu Ser Glu Asp His Tyr
            900                 905                 910

Lys Lys Tyr Leu Ala Lys Leu Arg Ser Ile Asn Pro Pro Cys Val Pro
        915                 920                 925

Phe Phe Gly Ile Tyr Leu Thr Asn Ile Leu Lys Thr Glu Glu Gly Asn
    930                 935                 940

Pro Glu Val Leu Lys Arg His Gly Lys Glu Leu Ile Asn Phe Ser Lys
945                 950                 955                 960

Arg Arg Lys Val Ala Glu Ile Thr Gly Glu Ile Gln Gln Tyr Gln Asn
                965                 970                 975

Gln Pro Tyr Cys Leu Arg Val Glu Ser Asp Ile Lys Arg Phe Phe Glu
            980                 985                 990

Asn Leu Asn Pro Met Gly Asn Ser Met Glu Lys Glu Phe Thr Asp Tyr
        995                1000                1005

Leu Phe Asn Lys Ser Leu Glu Ile Glu Pro Arg Asn Pro Lys Pro
    1010                1015                1020

Leu Pro Arg Phe Pro Lys Lys Tyr Ser Tyr Pro Leu Lys Ser Pro
    1025                1030                1035

Gly Val Arg Pro Ser Asn Pro Arg Pro Gly Thr Met Arg His Pro
    1040                1045                1050

Thr Pro Leu Gln Gln Glu Pro Arg Lys Ile Ser Tyr Ser Arg Ile
    1055                1060                1065

Pro Glu Ser Glu Thr Glu Ser Thr Ala Ser Ala Pro Asn Ser Pro
    1070                1075                1080

Arg Thr Pro Leu Thr Pro Pro Pro Ala Ser Gly Ala Ser Ser Thr
```

```
                1085                1090                1095

Thr Asp Val Cys Ser Val Phe Asp Ser Asp His Ser Ser Pro Phe
            1100                1105                1110

His Ser Ser Asn Asp Thr Val Phe Ile Gln Val Thr Leu Pro His
        1115                1120                1125

Gly Pro Arg Ser Ala Ser Val Ser Ser Ile Ser Leu Thr Lys Gly
        1130                1135                1140

Thr Asp Glu Val Pro Val Pro Pro Val Pro Arg Arg Arg
        1145                1150                1155

Pro Glu Ser Ala Pro Ala Glu Ser Ser Pro Ser Lys Ile Met Ser
        1160                1165                1170

Lys His Leu Asp Ser Pro Ala Ile Pro Pro Arg Gln Pro Thr
        1175                1180                1185

Ser Lys Ala Tyr Ser Pro Arg Tyr Ser Ile Ser Asp Arg Thr Ser
        1190                1195                1200

Ile Ser Asp Pro Pro Glu Ser Pro Pro Leu Leu Pro Pro Arg Glu
        1205                1210                1215

Pro Val Arg Thr Pro Asp Val Phe Ser Ser Ser Pro Leu His Leu
        1220                1225                1230

Gln Pro Pro Leu Gly Lys Lys Ser Asp His Gly Asn Ala Phe
        1235                1240                1245

Phe Pro Asn Ser Pro Ser Pro Phe Thr Pro Pro Pro Gln Thr
        1250                1255                1260

Pro Ser Pro His Gly Thr Arg Arg His Leu Pro Ser Pro Pro Leu
        1265                1270                1275

Thr Gln Glu Val Asp Leu His Ser Ile Ala Gly Pro Pro Val Pro
        1280                1285                1290

Pro Arg Gln Ser Thr Ser Gln His Ile Pro Lys Leu Pro Pro Lys
        1295                1300                1305

Thr Tyr Lys Arg Glu His Thr His Pro Ser Met His Arg Asp Gly
        1310                1315                1320

Pro Pro Leu Leu Glu Asn Ala His Ser Ser
        1325                1330

<210> SEQ ID NO 15
<211> LENGTH: 189
<212> TYPE: PRT
<213> ORGANISM: Homo sapiens

<400> SEQUENCE: 15

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110
```

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
            130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 16
<211> LENGTH: 170
<212> TYPE: PRT
<213> ORGANISM: Homo sapiens

<400> SEQUENCE: 16

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
            130                 135                 140

Ser Ala Lys Thr Arg Gln Gly Ser Arg Ser Gly Ser Ser Ser Ser Ser
145                 150                 155                 160

Gly Thr Leu Trp Asp Pro Pro Gly Pro Met
                165                 170

<210> SEQ ID NO 17
<211> LENGTH: 188
<212> TYPE: PRT
<213> ORGANISM: Homo sapiens

<400> SEQUENCE: 17

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

```
Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 18
<211> LENGTH: 189
<212> TYPE: PRT
<213> ORGANISM: Homo sapiens

<400> SEQUENCE: 18

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 19
<211> LENGTH: 189
<212> TYPE: PRT
<213> ORGANISM: Homo sapiens

<400> SEQUENCE: 19

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30
```

Asp Pro Thr Ile Glu Asp Ser Tyr Arg Lys Gln Val Ile Asp Gly
         35                  40                  45

Glu Thr Cys Leu Leu Asp Ile Leu Asp Thr Ala Gly Gln Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Ser Lys Ser Phe Ala Asp Ile Asn Leu Tyr
                 85                  90                  95

Arg Glu Gln Ile Lys Arg Val Lys Asp Ser Asp Val Pro Met Val
                100                 105                 110

Leu Val Gly Asn Lys Cys Asp Leu Pro Thr Arg Thr Val Asp Thr Lys
                115                 120                 125

Gln Ala His Glu Leu Ala Lys Ser Tyr Gly Ile Pro Phe Ile Glu Thr
130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
                180                 185

<210> SEQ ID NO 20
<211> LENGTH: 582
<212> TYPE: PRT
<213> ORGANISM: Homo sapiens

<400> SEQUENCE: 20

Met Thr Gln Gly Pro Gly Gly Arg Ala Pro Ala Pro Pro Ala Pro
 1                   5                  10                  15

Pro Glu Pro Glu Ala Pro Thr Thr Phe Cys Ala Leu Leu Pro Arg Met
                 20                  25                  30

Pro Gln Trp Lys Phe Ala Ala Pro Gly Gly Phe Leu Gly Arg Gly Pro
             35                  40                  45

Ala Ala Ala Arg Ala Ala Gly Ala Ser Gly Gly Ala Asp Pro Gln Pro
 50                  55                  60

Glu Pro Ala Gly Pro Gly Val Pro Ala Leu Ala Ala Val Leu
 65                  70                  75                  80

Gly Ala Cys Glu Pro Arg Cys Ala Ala Pro Cys Pro Leu Pro Ala Leu
                 85                  90                  95

Ser Arg Cys Arg Gly Ala Gly Ser Arg Gly Ser Arg Gly Gly Arg Gly
                100                 105                 110

Ala Ala Gly Ser Gly Asp Ala Ala Ala Ala Glu Trp Ile Arg Lys
                115                 120                 125

Gly Ser Phe Ile His Lys Pro Ala His Gly Trp Leu His Pro Asp Ala
130                 135                 140

Arg Val Leu Gly Pro Gly Val Ser Tyr Val Val Arg Tyr Met Gly Cys
145                 150                 155                 160

Ile Glu Val Leu Arg Ser Met Arg Ser Leu Asp Phe Asn Thr Arg Thr
                165                 170                 175

Gln Val Thr Arg Glu Ala Ile Asn Arg Leu His Glu Ala Val Pro Gly
                180                 185                 190

Val Arg Gly Ser Trp Lys Lys Ala Pro Asn Lys Ala Leu Ala Ser
             195                 200                 205

Val Leu Gly Lys Ser Asn Leu Arg Phe Ala Gly Met Ser Ile Ser Ile
210                 215                 220

His Ile Ser Thr Asp Gly Leu Ser Leu Ser Val Pro Ala Thr Arg Gln
225                 230                 235                 240

Val Ile Ala Asn His His Met Pro Ser Ile Ser Phe Ala Ser Gly Gly
            245                 250                 255

Asp Thr Asp Met Thr Asp Tyr Val Ala Tyr Val Ala Lys Asp Pro Ile
            260                 265                 270

Asn Gln Arg Ala Cys His Ile Leu Glu Cys Cys Glu Gly Leu Ala Gln
            275                 280                 285

Ser Ile Ile Ser Thr Val Gly Gln Ala Phe Glu Leu Arg Phe Lys Gln
            290                 295                 300

Tyr Leu His Ser Pro Pro Lys Val Ala Leu Pro Pro Glu Arg Leu Ala
305                 310                 315                 320

Gly Pro Glu Glu Ser Ala Trp Gly Asp Glu Asp Ser Leu Glu His
            325                 330                 335

Asn Tyr Tyr Asn Ser Ile Pro Gly Lys Glu Pro Leu Gly Gly Leu
            340                 345                 350

Val Asp Ser Arg Leu Ala Leu Thr Gln Pro Cys Ala Leu Thr Ala Leu
            355                 360                 365

Asp Gln Gly Pro Ser Pro Ser Leu Arg Asp Ala Cys Ser Leu Pro Trp
370                 375                 380

Asp Val Gly Ser Thr Gly Thr Ala Pro Pro Gly Asp Gly Tyr Val Gln
385                 390                 395                 400

Ala Asp Ala Arg Gly Pro Pro Asp His Glu Glu His Leu Tyr Val Asn
            405                 410                 415

Thr Gln Gly Leu Asp Ala Pro Glu Pro Glu Asp Ser Pro Lys Lys Asp
            420                 425                 430

Leu Phe Asp Met Arg Pro Phe Glu Asp Ala Leu Lys Leu His Glu Cys
            435                 440                 445

Ser Val Ala Ala Gly Val Thr Ala Ala Pro Leu Pro Leu Glu Asp Gln
450                 455                 460

Trp Pro Ser Pro Pro Thr Arg Arg Ala Pro Val Ala Pro Thr Glu Glu
465                 470                 475                 480

Gln Leu Arg Gln Glu Pro Trp Tyr His Gly Arg Met Ser Arg Arg Ala
            485                 490                 495

Ala Glu Arg Met Leu Arg Ala Asp Gly Asp Phe Leu Val Arg Asp Ser
            500                 505                 510

Val Thr Asn Pro Gly Gln Tyr Val Leu Thr Gly Met His Ala Gly Gln
            515                 520                 525

Pro Lys His Leu Leu Leu Val Asp Pro Glu Gly Val Val Arg Thr Lys
            530                 535                 540

Asp Val Leu Phe Glu Ser Ile Ser His Leu Ile Asp His His Leu Gln
545                 550                 555                 560

Asn Gly Gln Pro Ile Val Ala Ala Glu Ser Glu Leu His Leu Arg Gly
            565                 570                 575

Val Val Ser Arg Glu Pro
            580

<210> SEQ ID NO 21
<211> LENGTH: 480
<212> TYPE: PRT
<213> ORGANISM: Homo sapiens

<400> SEQUENCE: 21

Met Ser Asp Val Ala Ile Val Lys Glu Gly Trp Leu His Lys Arg Gly

```
1               5                   10                  15
Glu Tyr Ile Lys Thr Trp Arg Pro Arg Tyr Phe Leu Leu Lys Asn Asp
                20                  25                  30

Gly Thr Phe Ile Gly Tyr Lys Glu Arg Pro Gln Asp Val Asp Gln Arg
                35                  40                  45

Glu Ala Pro Leu Asn Asn Phe Ser Val Ala Gln Cys Gln Leu Met Lys
 50                      55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
                100                 105                 110

Gln Glu Glu Glu Met Asp Phe Arg Ser Gly Ser Pro Ser Asp Asn
                115                 120                 125

Ser Gly Ala Glu Glu Met Glu Val Ser Leu Ala Lys Pro Lys His Arg
 130                     135                 140

Val Thr Met Asn Glu Phe Glu Tyr Leu Lys Leu Leu Gly Lys Gly Thr
145                  150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
                180                 185                 190

Ala His Thr Leu Thr Glu Asn Arg Val Leu Gln Asn Ser Arg His Pro
                195                 200                 205

Phe Leu Thr Ala Leu Lys Tyr Ser Phe Gln Thr His Asp Arg Leu Cys
210                  215                 220

Phe Val Met Glu Tyr Ala Asn Gly Gly Glu Leu Phe Phe His Leu Ser
225                  230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
                260                 265                 270

Arg Asp Leu Lys Leu Glu Asn Leu Met Leu Asp Lys Asp Gly His Ile
                275                 280                 285

Lys Ile Thr Asp Phe Gly Leu Cys Lys Glu Gly Ile Lys Asp Gly Ala
                290                 295                 300

Thr Met Lys Thr Phe Cys Gly Thr Pro Glu Tyr Leu Ala Pro Glu Val
305                  310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
                340                 345                 350

Asp His Glu Lys Leu Phe Glu Leu Ile Leu Met Glu Glu Ile Arg Phe
                355                 360                 365

Pro Arg Thr Leu Gly Pro Glu Ala Lys Ser Leu Leu Ser Gly Leu Leu
                370                 375                 380

Lys Lys Asp Pro Lys Gln Arg Leu Gly Gly Gly Ser Glu Asp Ala Lys
385                  390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
                420                 425                 430
```

```
Thr Asp Thr Arg Tyr Phe Asp Glu Glu Phe Thr Ala Gln Met Ile Thr
            435                 440                 445

Ile Thr Pro Pro Asp Gln Asp Ser Met Glu Cys Val Asp Ser Glu
450                 455                 460

Arg Arg Pro His Phe Pro Gln Phe Ser Tyr Ser Ala Ser Gly Thr Ala
465                 470                 475                 480

<210> SEQ ID NO 22
<211> LENGTH: 481
<212> TYPE: PRT
<213> ORGANISM: Homo sapiens

<400> SEQUENCE: 22

Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp
            20                  25                  30

Gly Ser Phe Ile Gly Tyr Lys Glu Arg Pro Glu Ala Pro Asp Gln Thr
        35                  40                  45

Leu Pro Pro Leu Asn Asn Phe Ser Val Ala Glu Cys Gln Leu Met Lys
50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
        115                 120                 125

Asp Ser Ser Thr Thr Glu Glu Met Glu Val Ala Val Ser Lys Ala Arg
130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
            180                 185                 190

Glu Val Ala His Thr Val Thr Glu Ser Arg Val Leu Gln Asn Thr Arg
        195                 200                 205

His Pro Phe Leu Thr Ala Leu Lys Tyr Ala Phe Gln Thr His Asp Arg
210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
            260                 265                 270

Tyr Arg Asp Ile Lys Leu Glu Asn Leu Met Leu Asp Lys Asp Gly His
        275                 280                 285

Ile Lys Ile Thr Asp Phe Gly Leu Cys Lys Glu Gly Ile Ser Asp Gly
290                 295                 300

Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
```

```
                    325                 330                 335
Gly Val Val Met Tyr Glu Met Met Cys Gly Arg Leu Pro Phe Tyr Asn
                340                 345                 350
Gln Asp His Glu Arg Leu Phe Glu Leu Ile Leu Met Glu Glu Ile Arg
            355                 360                 365
Phe Pro Arg Thr Leu Ser Pro Glu Ala Lys Ser Leu Leu Ala Gly Leu
        370                 375                 380
Leu Lys Lys Asp Pro Lys Gln Arg Leu Gly Gly Gly Pro Ser Asp Ala
385                 390                 395                 400
Lys Glu Val Met Glu His Arg Phe Phe Leu Ser Ile Asn Trp Gln Asp
                405                 410                 415
Val Val Gln Lys Lys Leu Leu Pro Pro Phe Lys Pro Gln Val Thr Ser
                420                 425                 430
Glu Val Asp Thr Arg Tyr Phe Asp Asp Glu Phe Thr Ala Gln Ser Ile
                435                 440                 445
Thr Ile Thr Pro Pro Asp Arg Tyr Asp Ser Leu Gly Leu Leu Glu Leu
450                 455                 460
Asp Gln Arg Thr His Phe Pro Gln Phe Ser Tyr Ser Ala Ser Ile Arg
465                 470                 475                 480
Glu

<210> SEQ ID NO 23
<211> LENGTH: 479
<212> TYPE: PRT
<213> ORGANISM: Homo sapiens

<400> SEQUENCE: 23

Met Ser Asp Val Thr Ile Val Lys Glu Gly Trp Val Gln Lys Arg Gly
1               5                   10                  15
Glu Tyr Ile Lys Asn Trp Arg Pro Arg Tyr Phe Leu Leu Lys Thr Asp
                20                  25                  30
Gly Ser Phe Ile Gly Tyr Lys Glu Lys Pro Gln Asp Val Asp Leu Pro
            35                  40                  45
Tyr Pro Leu Asn Asn Phe Ser Val Ala Lys Cys Gln Leu Met Lys Thr
        50                  55                  60
Glu Arg Pro Lys Pro Asn Thr Phe Ile Ile Arg Cys Leu Gln Trp Thr
65                  70                  75                  80
Thr Val Ile Glu Arg Thr Phe His Val Asp Thr Pro Glu Glu Arg Glu
                85                  90                  95
Glu Trp Thr Glu Ala Ile Gln Ala Val Ala Asp Arg Leu Gln Arg Gln
            100                 105                 110
Glu Glu Glu Arg Met Asn Cys Ser Pro Thr Ser Gln Ile Asp Asn Ile
        115                 120                 125
Gly Glu Glu Glu Met Asp Ala Ser Thr Thr His His Lys Arg Lys Thr
130                 135                 140
Met Asn Asp Phe Asp Tyr Leu Lys Leu Leu Gly Lys Gly Thr Phe Gly
145                 150                 155                 160
Lys Val Ile Leu Val Arg Glu Lys Ala Ser Gly Lys Tyr Tyr Ala Met
                165                 170                 175
Lys Ile Leu Lys Lys Glu Val Ile Ile Ala Lys Asp Glu Val Ala His
            180                 185                 190
Thr Leu Thr Glu Ser Arg Val Leu Lys Asn Thr Arg His Pro Phe Leu
        195                 200                 205
Thr Ser Leu Lys Tyr Ser Phe Gln Thr Lys Asp Arg Leu Cys Phe Val
```

```
                210                 215                 220
Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
                260                 265                 270

Lys Leu Glu Asn Leu Met Leu Asp Lys Asp Gly His Ile Lys Ile Thr
                275                 280                 285

Asp Phe Gly Leu Cys Lys Glu Gly Ile Thr Asp Ala Ala Thr Met Lys
                290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
                340                 345                 350

Lys Leu Phe Glu Leu Ile Leu Met Glu Asp Ile Lys Phe Pro Arg Thr
                355                 360                 365

Leu Ser Ser Asp Ala Lys Ser Leu Leu Ser Gly Leu Leu Ile Lys Asp
370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
                420                 425                 430

Arg Tyr Phe Asp Glu Glu Phe Thr Ala Gln Thr Ile Thr Ile Thr Pro
                435                 440                 445

Pro Glu Lys Tyr Asp Glu Asp Gly Met Asp Cys Met Asp Asn Glu Arg
                450                 455                 460

Arg Pro His Phe Pro Gln Phe Ser Tyr Ser Ala Ser Gly Arg Glu
465                 470                 475

<210> SEQ ID NO 24
<211> LENGTH: 465
<212> TYPE: PRT
<213> ORGANISM: Homo sapiens

<400> SEQUENCE: 24

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
                20                  25                  30

Gly Ser Phe Ile Gly Tyr Lys Glu Lys Pro Gln Asp Val Asp Leu Pro
            35                  40                  45

Tyr Pro Leu Asn Asn Phe Ser Val Ala Lys Cys Gln Leu Met Lys Thr
    50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
            100                 105                 110
```

```
Glu Glu Glu Arg Met Asn Cys Ser Pro Thr Ser Gln Ile Asp Asn Ile
            115                 120                 125

Gly Glu Glu Met Asp Ala Ser Thr Thr His His Lys Arg Lys Thr
    130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                    165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
            195                 200                 205

Thr Ser Leu Lys Tyr Ser Phe Gln Thr Lys Asp Arg Leu Cys Phe Val
            210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                    245                 250                 255

Ser Ala Leu Asp Tyr Leu His Ser Gly Lys Ile Val Tyr Arg Asp Leu
                260                 265                 270

Lys Leu Glu Asn Leu Met Leu Asp Lys Asp Gly His Ile Lys Ile Thr
            275                 280                 285

Asp Phe Gly Leu Cys Lys Glu Gly Ile Thr Asp Ala Ala Thr Met Lys
290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
                340                 345                 350

Lys Leu Phe Glu Leu Ile Leu Met Glu Asp Ile Lys Phe Pro Arg Thr
            355                 360                 365

Leu Ser Ser Asp Ala Lys Ser Leu Leu Ser Gly Leu Leu Ile Lys Asp
    370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
                420                 425                 430

Arg Tyr Phe Asp Glu Glu Phe Thr Ala Gln Thr Ile Thr Ile Thr Pro
                435                 440                 445

Pro Glu Lys Cys Gln Gln Ser Asp Cys Gly Met Leu Gly Asn Trp Lys
    450                 455                 460

Lys
465
```

COMPOUNDS INHIBITING CD95 SIGNALING FOR THE TREATMENT OF PANCREATIC CANCER

The present invention is concerned with compounds inhibiting CD95 signaling in pancreatic cancer cells. Furthermore, contemplated by the current invention are medicaments comprising such a compound for the prevention and/or treatment of pancreatic cancer as well as the use of such a compound for the manufacture of a medicament for the prevention and/or treatment of pancreatic cancer, the prevention of migration of cancer cells, and/or the prevention and/or treatment of an inflammatory reaction. The present invention also refers to a method for the identification of a compound inhibiting CD95 signaling, as well as to a method for the manufacture of a medicament comprising the steps of the method for the identification of a compound inhibiting CD95 signaling and the further step of formulating the inhibiting compound as a medicament.

CD95 (synonyms: FasR, Apo-1) is a receptor on the surface of mammalian cells, which has been, known to have the capacity to induce apoptosis upon binding of the trimeric form of its cognate ligand, CD95L (Krammer, P. H. (2000). CD95's deadly mission in the immune system. Nature 407, 789-795). Furthermore, the CD95/CD95L- system was found to be used by malignant cells to increase their invasive and their metastatic capacity. In this pathway, CD95 activation increases invasion by activating the PI3K pathway, leading to an increased expression of metalloproteinases (Kleber, S., et al., (2008). Yes and PI3K bind CD95 to signal invasion of glioblastoma. Cancer Cell 13, 235-248).

In a glioma model, it was found that the consequences of CD95 activation were dependent on the staging of the tumor: CD95 activation caused apoptosis only in low-grade tumor cells (WHO grade I and II), whereas cells from high-grade (grade IV) tumors were resistant to apoptosis. What is more, in the high-grade cells migration and invasion were activated by CD95 activation (Kleber, S., et al., (2008). Yes and PI3K bind CD95 to signal invasion of glioblastoma. Cancer Cell 13, 235-248).

Pancreatic cancer has an incidence of approximately 10 to 13 cases per 100,000 subjects and year; of these, 95% are pancreatic adenocarcinoma. This cancer is associated with a very poor prognosis, which is mainly caused by the fact that patients usually have very long initial symptom-free periods. As a consequence, only 7% of pancreatic cancer cases are diagnosed while the cancer is still confined to the primary site (localized stage), whereas more than 50% are diagnosed only after the cancer has already metastasized (distant stage). The corresponding relative 5-year survival rates are 22% for localized stage and less than 2% for distant stage, respectively.

For pancreatic cancer patients not eligible for surgical resection with curative intent, no curative treatment is available at all. Chemotherapy regimens using Gemcitabine have been devised, but due to the high resistance of pancreatic cancer cells to chemotherapy they are used mainly as a palliative measure to improve patients' quality of life. The impact of various chemotherapy and/or radiotherapy regimens on survival is in the range of months, so prognosis is not improved significantly by such treatments (Pawlik, T. M., et al., (2008). Evaluating the impact of a single-day multidisciplinary clinic on the management of pancreatic cancer. Ann. Surg. Oncol. 15, 2081-2088.). So there is a need in the art for improved therapies of pancreatic cancer and for new compounds that may prove useful in the treatment of this cancer.

The present invention, now, relates to a compound inhibiting CD95 signaling in a pancreatic cancer cell.

The term "CD95 signaling" as used in this specification, preferably, relates to the transmission of at least one activity modulating signal from one component of the CD95 signaling pathway to another in pancreatic cancer cells. It is to be understood that CD95 signaling as used herein specifically relates to the transmission of activity modulating signals that are transmitted via or generated by CD95 and transmitted via the interaction of CD95 with Sck (alternative name: SHC2, Src Homology-2 Domain Containing Transforming Protein) in a pancreatic cancer cell. Preferred components of the CD95 signaling pathway are described elsewhere herein. Preferably, the activity modulating signal is an activating signal. It is to be understood, however, that the inactivation of one of the components of a signaling pathway may also lead to an activation of this signaling pathway as a whole, so the activity modulating signal transmitted may also be an inhibitory signal. The modes by which activity modulating signals are transmitted comprise, e.g., protein-protein interaction, induction of isomerization, proteolytic processing, intracellular translocation and/or transfer of at least one Ubiquitin moiety. Preferably, transmission of an activity modulating signal comprises transfer of at least one small molecule group, like, e.g., a sulfate, a phosphate, an acyl, a methyl, or a prenyl group. In pancreatic tumor cells, the upstream cascade of molecular events after CD95 stimulation is driven by the non-catalytic adaptor protein Sck. CD95 stimulation leads to increased Sck tyrosine phosphorylation and activation of PI3K and ERK, thereby leading to increased migration.

A "signaling component of the CD95 signaling pathway" (CD95 signaling component) in the context of the present invention, preferably, is a chemical molecule involved in the generation and/or intra- or extracellular transmission of an activatory signal transmitted via or generated by CD95 and transmitted via SHC as described herein above in a pancreatic cancer cell. Preferably, said CD95 signaling component is a protein. More preferably, said CD95 signaling component is selected from the group consisting of CD95 Ligand (Seq ID NO:1, Genbank Acc No: NP_000630.1 GI:4557329), CD95 (Seq ID NO:2, Genbank Acc No: AAH12479.1 GI:15214692), the SFK (Src family kinases) (B lymphoid tyrosine kinase, Seq ID NO: 3, Genbank Ace No: NP_001706.2 GI:33469982; Yamaguchi sarcoma viral (v-yes-1) oncogene homolog isoform A, Seq ID NO: 4, Genbank Acc No: NP_002341.1 GI:4505055; Yamaguchi sarcoma viral (v-yes-1) oncogene homolog isoform B, Seq ID No: 5, Genbank Ace No: NP_001104567.1 GI:162287326; hemopoietic cell kinase isoform p61HCK, Seq ID NO:6, Genbank Ace No: NP___002101.2 GI:30795229; proto-oncogene tyrosine-protein kinase SRC, Seq ID NO: 7, Genbank Acc No: NP_938033.1 GI:38202217; proto-oncogene tyrosine-protein kinase FGR, Seq ID NO: 8, Genbank Ace No: NP_001036212.1 GI:112382244; lymphocyte-specific protein tyrosine kinase precursor, Seq ID NO: 9, Genbank Acc No: NP_001036236.1 GI:112789548; proto-oncogene tyrosine-protein kinase fyn isoform c, Seq ID NO: 10, Genbank Acc No: NP_694593.1 GI:23510364; and viral oncogene yes-1 homolog 1, Seq ID NO: 11, Genbank Acc No: NP_05424.1 GI:4885661), Grb2 (Growth Factor Receptor Bound protein-2) (growth factor receptor-bound protein 2 isoform 1, Seq ID NO: 12, Genbank Acc No: NP_002077.1 GI:4504111; growth factor receptor-bound protein 2 isoform 2, Seq ID NO: 13, Genbank Acc No: NP_987102.1 GI:45359859), SOS (Son of Sevenless) (son of sevenless homolog 1, Seq ID NO: 14, Genbank Acc No: NP_05624.2 GI:15529996), and the small GTP binding proteins of the Ras family (v-Ha-ras Harvey rat sarcoma viral oncogene homolog isoform 1, Seq ID NO: 15, Genbank Acc No:

NP_001123914.1 GI:194363762; v-Ha-ras Harvey rat sarcoma viral oncogene homolog isoform 2, Seq ID NO: 16, Genbank Acc No: NP_789765.1 GI:34222246; c-K-ras2 protein isoform b precursor, Seq ID NO: 17, Genbank Acc No: NP_004976.2 GI:15718761; c-K-ras2 protein isoform a precursor, Seq ID NO: 18, Genbank Acc No: NP_203524.1 GI:15718763; neuroblastoma RAS viral (v-ras) oncogene homolog precursor, Seq ID NO:19, Genbank Acc No: NP_002515.1 GI:4505451). Most preferably, said CD95 signaling component is Sck (SHC (Src homology 2 domain containing) transforming protein 2, Seq ID NO: 20, Genbank Acc No: NP_036567.2 GI:169790811).

The term "compound" refers to a chemical molecule, i.e. any organic or inorganic substance. The organic molecule may belong to any known chemical class of molecules. Preferably, organic molecules are lipids, fatty acids, purines, pyrimidines, alkaloids, amino acids, peptides, polypeptides, proteins, biogenic amines, isoprenoids or steroids.

The term "compound inhibiting CD95 signaling" as used herein relates to a compound that, when brought into contact with a pancreatic cancer cell, causes a change in the expression of at least one gene coding for a CD95 signaling component (CD95 signaling gene) and/or in the activity and/or stability of at least one of the gene products of said CD95 signaling gene. Said change is to such an extent that said pancreatic cancer cell becomes measurably differentiated from a control cell not brought into contact with said compound. Parameters that can be determined in order to detect inhibition of CD95 signaling include cell proliferation, cell migration, production of metalloproteinases by the cell, metastasis formation, and tumor invasiveness. The activity of a gene product of a CD95 signaling gene is its capacity to contribute to the transmission of activity modulating signals in CD95 signaling as described herein above. The stability of a gene product of a CD95 signaling gene is its degree of resistance to loss of activity or to disintegration. The stability of a gene product can be measured by determining the time required until the number of molecules or the activity of said molecules has decreased to a certain fraction of the initial value, e.g. 0.5, 0.2, or 0.1. E.g, the time required to reduce the amount or the activity of a given population of molecules to 0.5 is the half-life period; thus, a longer half life period indicates increased stability. Methods for determining a change in activity or stability of a gene product will depend on the nature of such gene product; such methods may comprise, e.g., determining the amount of a polynucleic acid by hybridization or PCR methods well known to the skilled artisan, or measuring specific enzymatic activity in e.g. a kinase assay as described herein below (see, e.g. Example 5).

Preferably, the compound inhibiting CD95 signaling negatively interferes with, i.e. inhibits, the function of at least one of the said CD95 signaling genes or their gene products, meaning that it, preferably, decreases expression of said at least one gene or decreases the activity and /or stability of at least one of the products of said at least one gene. However, since increase of expression or activation of a single CD95 signaling component may lead to the overall inhibition of CD95 signaling as detailed in this specification above, the compound inhibiting CD95 signaling may also activate the function of at least one of the said CD95 signaling genes or their gene products.

It is to be understood that modulating the function of a gene or its gene products refers to statistically significant modulations of the function, i.e. it can refer to modest changes in the function of a gene or its gene products, meaning a change in amount, activity, or half-life of 10% or more, 20% or more, 30% or more, 40% or more, or 50% or more. Also, in the case of inhibition of CD95 signaling, inhibition of the function of one of the genes coding for a component mediating CD95 signaling to an extent leading to a fraction of at least 10%, at least 15%, at least 20%, at least 30%, at least 40%, at least 50% of cells having non-functional CD95 signaling is appropriate. Whether modulation is statistically significant can be determined by the skilled artisan without further ado, preferably, by applying standard statistics such as, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001.

It is contemplated by the current invention that suitable compounds may preferably be obtained by screening artificial chemical libraries obtained, e.g., by combinatorial chemistry approaches or by screening of natural compound libraries obtained, e.g., by fractioning extracts from biological organisms such as archea, bacteria, funghi, plants, or animals. Suitable compounds can also be generated by in silico screening methods based on, e.g., molecular modelling approaches.

Preferably, compounds modulating the function of a CD95 signaling gene are identified by using assays such as migration assays or determining induction of phosphorylation of downstream targets, such as ERK or AKT. More preferably, said technologies are used in high-throughput screening systems (see, for example, Liu et al. (2004), Am. J. Pharmacogenomics 4(4), 263-276).

Preferably, compounds inhibiting CD95 signaling are selected from a list consisting of RNA interference (RNAi) agents, ribozymes, DNAzymes, inhibitory antibodies, and aptamers. Methods of obtaining such compounds are well known in the art (see e.g. Bhindi et al. (2007), Am. J. Path. 171, 1079-1088, and the remainder of this specification).

"RNA interference" refers to sequence-specific, post-transcriptional gene silencing of a selected target gene. The RNAi agents in the context of the present invention, preferably, reduce the expression of a CD95 signaling gene by degradation of RNA transcribed from said CD95 signaling gene (target RNA) or by inhibition of translation of said target RNA. Target RNAs preferably are mRNAs coding for CD95 signaling components, however, any type of RNA is encompassed by the RNAi methods of the invention. It is to be understood that silencing as used herein does not necessarily mean the complete abolishment of gene expression in all cases. RNAi, preferably, reduces gene expression by at least 50%, at least 60%, at least 70%, at least 80%, at least 90%, at least 95%, at least 98%, or at least 99% as compared to the expression level in a reference without RNAi.

RNAi requires in the cell the presence of dsRNAs that are homologous in sequence to the target RNAs. The term "dsRNA" refers to RNA having a duplex structure comprising two complementary and anti-parallel nucleic acid strands. The RNA strands forming the dsRNA may have the same or a different number of nucleotides, whereby one of the strands of the dsRNA can be the target RNA. It is, however, also contemplated by the present invention that the dsRNA is formed between two sequence stretches on the same RNA molecule.

RNAi may be used to specifically inhibit expression of CD95 signaling genes of the present invention in vivo. Accordingly, it may be used for therapeutic approaches to treat pancreatic cancers which are accompanied with an altered expression of at least one of the CD95 signaling genes of the present invention. For such therapeutic approaches, expression constructs for siRNA may be introduced into target cells of the host which suffer from altered CD95 signaling gene expression. Accordingly, siRNA may be combined efficiently with other therapy approaches.

Methods relating to the use of RNAi to silence genes in animals, including mammals, are known in the art (see, for example, Hammond et al. (2001), Nature Rev. Genet. 2, 110-119; Bernstein et al. (2001), Nature 409, 363-366; WO 9932619; and Elbashir et al. (2001), Nature 411: 494-498).

As used herein, the term "RNAi agent", preferably, refers to a siRNA agent or an miRNA agent as specified herein. The RNAi agent of the present invention is of sufficient length and complementarity to stably interact with the target RNA, i.e. it comprises at least 15, at least 17, at least 19, at least 21, at least 22 nucleotides complementary to the target RNA. By "stably interact" is meant interaction of the RNAi agent or its products produced by the cell with a target RNA, e.g., by forming hydrogen bonds with complementary nucleotides in the target RNA under physiological conditions.

Not all nucleotides of an RNAi agent necessarily exhibit complete Watson-Crick base pairs in the interaction with the target RNA; the two RNA strands may be substantially complementary. Preferably, complementarity between the RNAi agent and the RNA target is 100%, but can be less if desired, preferably 91%, 92%, 93%, 94%, 95%, 96%, 97%, 98%, or 99%. For example, 19 bases out of 21 bases may be base-paired. In some instances, where distinction between various allelic variants is desired, 100% complementarity to the CD95 signaling gene may be required in order to effectively discern the target sequence from the other allelic sequence. When selecting between allelic targets, choice of length is also an important factor because it is the other factor involved in the percent complementary and the ability to differentiate between allelic differences.

The term "siRNA agent" as meant herein encompasses: a) a dsRNA consisting of at least 15, at least 17, at least 19, at least 21 consecutive nucleotides base-paired, i.e. forming hydrogen bonds with a complementary nucleotide. b) a small interfering RNA (siRNA) molecule or a molecule comprising an siRNA molecule. The siRNA is a single-stranded RNA molecule with a length, preferably, greater than or equal to 15 nucleotides and, preferably, a length of 15 to 49 nucleotides, more preferably 17 to 30 nucleotides, and most preferably 17, 18, 19, 20, 21, 22, 23, 24, 25, 26, 27, 28, 29, and 30 nucleotides. c) a polynucleic acid encoding a) or b), wherein, preferably, said polynucleic acid is operatively linked to an expression control sequence. Thus, the function of the siRNA agent to inhibit expression of the CD95 signaling gene can be modulated by said expression control sequence. Preferred expression control sequences are those which can be regulated by exogenous stimuli, e.g. the tet operator, whose activity can be regulated by tetracycline, or heat inducible promoters. Alternatively or in addition, one or more expression control sequences can be used which allow tissue-specific expression of the siRNA agent.

It is, however, also contemplated by the current invention that the RNAi agent is a miRNA agent. A "miRNA agent" as meant herein encompasses: a) a pri-microRNA, i.e. an mRNA comprising at least 30, at least 40, at least 50, at least 60, at least 70 nucleotides base-paired to a complemetary sequence on the same mRNA molecule ("stem"), i.e. as a dsRNA, separated by a stretch of non-base-paired nucleotides ("loop"). b) a pre-microRNA, i.e. a dsRNA molecule comprising a stretch of at least 19, at least 20, at least 21, at least 22, at least 23, at least24, at least 25 base-paired nucleotides formed by nucleotides of the same RNA molecule (stem), separated by a loop. c) a microRNA (miRNA), i.e. a dsRNA comprising at least 15, at least 17, at least 18, at least 19, at least 21 nucleotides on two separate RNA strands. d) a polynucleic acid encoding a) or b), wherein, preferably, said polynucleic acid is operatively linked to an expression control sequence as specified above.

As used herein, the term "ribozyme" refers to an RNA molecule specifically hybridizing to a target RNA molecule and catalysing the hydrolysis of one or more phosphodiester bonds in said target RNA molecule, causing the target RNA to be degraded by cellular enzymes. RNA sequences showing suitable catalytic properties, like hammerhead ribozyme, hairpin ribozyme, or RNase P are known in the art (see, e.g. Doherty and Doudna (2001), Annu. Rev. Biophys. Biomol. Struct. 30, 457-475). Sequence specificity and, thus, target RNA specificity is accomplished by specific binding of the ribozyme to the target RNA by means of Watson-Crick base pairing of complementary, anti-parallel RNA strands. Methods of generating ribozymes directed against RNA sequences of interest are known in the art (see, for example, Citti and Rainaldi (2005), Curr. Gene Ther. 5(1), 11-24).

The term "DNAzyme" refers to a single-stranded DNA molecule having the same binding and catalytic properties as a ribozyme, however, said DNAzyme comprises desoxyribonucleotides instead of ribonucleotides. Methods of generating DNAzymes, like in vitro selection, are known to the one skilled in the art (see, e.g. Achenbach et al. (2004) Curr. Pharm. Biotechnol. 5(4), 321-336).

It is, however, also contemplated by the current invention that the ribozyme or DNAzyme comprises modified nucleotides or compounds modifying the stability, specificity, or catalytic properties of said ribozymes or DNAzymes. It is to be understood that "catalysing" as used herein does not necessarily mean the promotion of more than one hydrolysis event per molecule of ribozyme or DNAzyme.

The term "antibody" as used in this specification refers to a molecule from the subgroup of gamma globulin proteins which is also referred to as the immunoglobulins (Ig). Antibodies can, preferably, be of any subtype, i.e. IgA, IgD, IgE, IgM or, more preferably, IgG. Antibodies against polypeptides encoded by CD95 signaling genes of the invention can be prepared by well known methods using a purified polypeptide or a suitable fragment derived therefrom as an antigen. A fragment which is suitable as an antigen may be identified by antigenicity determining algorithms well known in the art. Such fragments may be obtained either by proteolytic digestion from polypeptides encoded by CD95 signaling genes or may be synthetic peptides. Preferably, the antibody of the present invention is a monoclonal antibody, a polyclonal antibody, a single chain antibody, a human or humanized antibody or primatized, chimerized or fragment thereof. Also comprised as antibodies of the present invention are a bispecific or a trispecific antibody, a synthetic antibody, an antibody fragment, such as Fab, Fv or say fragments etc., or a chemically modified derivative of any of these. An antibody of the present invention preferably binds specifically (i.e. does not cross react with other polypeptides or peptides) to one of the polypeptides of the invention. Specific binding can be tested by various well known techniques.

Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature 256 (1975), 495, and Galfre, Meth. Enzymol. 73 (1981), 3, which comprise the fusion of mouse or other rodent myeloma cells to spleen cells derived from immunized mammals.

The term "inhibitory antibody" relates to an antibody inhibiting the activity of a polypeptide encoded by a CD95 signaling gene referred to in accordance with the present invention. Said inhibition preferably is caused by binding of the inhibitory antibody to an active center or to an interaction site of a polypeptide of the invention, causing an inhibition of CD95 signaling in the cell treated with said inhibitory antibody. The person skilled in the art knows means and methods to obtain inhibitory antibodies to specific proteins, like e.g. the method proposed by Rosen and Koshland (1988), Anal. Biochem. 170(1), 31-37. It is to be understood that inhibiting as used herein does not necessarily mean the complete abolishment of activity in all cases Inhibitory antibodies, preferably, reduce CD95 signaling by at least 10%, at least 20%, at least 30%, at least 40%, or at least 50% as compared to a reference.

In the context of this invention, an "aptamer" is an oligo-nucleic acid or a peptide specifically binding to a polypeptide encoded by one of the CD95 signaling genes of the present invention and modifying the activity and/or stability of said polypeptide encoded by one of the CD95 signaling genes. Peptide aptamers, preferably, are peptides comprising 8-80 amino acids, more preferably 10-50 amino acids, and most preferably 15-30 amino acids. They can e.g. be isolated from randomized peptide expression libraries in a suitable host system like baker's yeast (see, for example, Klenenz et al. (2002), Cell. Mol. Life Sci. 59, 1993-1998). Peptide aptamers, preferably, are used as free peptides; The peptide aptamers of this invention also include chemically modified peptide aptamers, e.g., peptide aptamers containing modified amino acids or peptide aptamers which are, e.g., biotinylated, or are coupled to fluorophores, such as fluorescin, or Cy 3, are conformationally restricted, e.g. by disulfide bridging or by stapling (Walensky 2004, Science 305(5689): 1466-1470), or are linked to cell penetration peptides or protein transduction domains (Snyder 2004, Pharm Res 21(3): 389-393). Such modifications may improve the biological properties of the peptide aptamers, e.g., cell penetration, binding, stability, or may be used as detection labels. The peptide aptamers of the present invention can be recombinantly manufactured or may be chemically synthesised. The peptide aptamers may comprise further amino acids which may serve as a tag for purification or detection. Moreover, the peptide aptamers of the present invention may be comprised by a fusion polypeptide, wherein the fusion partner may e.g. serve as a "scaffold", fixing the peptide aptamer in a defined conformation. The variant or modified peptide aptamers, preferably, retain the biological activity of the peptide aptamers, i.e. they are capable of specifically binding to a polypeptide encoded by one of the CD95 signaling genes of the present invention. These properties can be tested by the assays described in the accompanying Examples below.

An RNA or DNA aptamer is an RNA or DNA molecule that is able to specifically bind to the three-dimensional surface of a polypeptide and to inhibit the function of said polypeptide. RNA or DNA aptamers can be obtained e.g. by in vitro selection, e.g. systematic evolution of ligands by exponential enrichment (SELEX). Methods relating to the development and use of RNA and DNA aptamers are known in the art (see, for example, Ulrich (2006), Handb. Exp. Pharmacol. 173, 305-326 and Ulrich (2005), Med. Chem. 1(2), 199-208).

Also encompassed as compounds inhibiting CD95 signaling in the present invention are fusion proteins comprising at least one first domain comprising a ligand-binding domain of CD95 fused to a heterologous second domain comprising at least a portion of a constant immunoglobulin domain. The fusion protein may be a monomeric protein or a multimeric protein, e.g. a dimeric, trimeric, or tetrameric protein. Multi-mers may consist only of fusion protein molecules as described above, i.e. be homodimers, homotrimers, homotetramers or the like. It is, however, also contemplated by the current invention that the multimers may comprise other proteins as well. Multimerization may be facilitated via the constant immunoglobulin region of the fusion protein. The fusion protein may, however, also comprise additional domains mediating multimerization, e.g. a tenascin trimerization domain. In a preferred embodiment, the first and the second domain overlap by at least one amino acid in the fusion region.

"Cancer" in the context of this invention refers to a disease of an animal, preferably man, characterized by uncontrolled growth by a group of body cells ("cancer cells"). This uncontrolled growth may be accompanied by intrusion into and destruction of surrounding tissue and possibly spread of cancer cells to other locations in the body. The term "pancreatic cancer" refers to a cancer wherein the cells forming the cancer are part of or originate from the pancreas of a mammal, preferably a human. Most preferably, the pancreatic cancer is an adenocarcinoma of pancreatic origin.

Advantageously, it has been found in the context of the present invention that inhibition of CD95 signaling in pancreatic cancer cells leads to a decrease in the migratory, and thus, metastatic potential of said pancreatic cancer cells. Thus, the compounds of the present invention are well suited for the prevention of tissue invasion and metastasis formation by pancreatic cancer cells.

The definitions made above apply mutatis mutandis to the following:

Moreover, the present invention also relates to a medicament comprising a compound as specified above for the prevention and/or treatment of pancreatic cancer.

The term "medicament" as used herein comprises the compounds of the present invention and optionally one or more pharmaceutically acceptable carrier. The compounds of the present invention can be formulated as pharmaceutically acceptable salts. Acceptable salts comprise acetate, methylester, HCl, sulfate, chloride and the like. The medicaments are, preferably, administered topically or systemically. Suitable routes of administration conventionally used for drug administration are intratumoral, peritumoral, oral, intravenous, or parenteral administration as well as inhalation. However, depending on the nature and mode of action of the compound, the medicaments may be administered by other routes as well. For example, polynucleotide compounds may be administered in a gene therapy approach by using viral vectors, viruses or liposomes.

Moreover, the compounds can be administered in combination with other drugs either in a common medicament or as separated medicaments wherein said separated medicaments may be provided in the form of a kit of parts.

The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the medicament or formulation may also include other carriers, adjuvants, or nontoxic, nontherapeutic, nonimmunogenic stabilizers and the like.

A therapeutically effective dose refers to an amount of the compounds to be used in a medicament of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg; however, doses below or above this exemplary range are envisioned, especially considering the aforementioned factors. Generally, the regimen as a regular administration of the medicament should be in the range of 1 µg to 10 mg units per day. If the regimen is a continuous infusion, it should also be in the range of 1 µg to 10 mg units per kilogram of body weight per minute, respectively. Progress can be monitored by periodic assessment. However, depending on the subject and the mode of administration, the quantity of substance administration may vary over a wide range to provide from about 0.01 mg per kg body mass to about 10 mg per kg body mass.

The medicaments and formulations referred to herein are administered at least once in order to treat or ameliorate or prevent a disease or condition recited in this specification. However, the said medicaments may be administered more than one time, for example from one to four times daily up to a non-limited number of days.

Specific medicaments are prepared in a manner well known in the pharmaceutical art and comprise at least one active compound referred to herein above in admixture or otherwise associated with a pharmaceutically acceptable carrier or diluent. For making those specific medicaments, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

The term "treatment" refers to amelioration of the disease (pancreatic cancer) referred to herein or of the symptoms accompanied therewith to a significant extent. Said treatment as used herein also includes an entire restoration of the health with respect to the diseases referred to herein. It is to be understood that treatment as used in accordance with the present invention may not be effective in all subjects to be treated. However, the term shall require that a statistically significant portion of subjects suffering from a disease referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population.

The term "prevention" refers to retainment of health with respect to the disease (pancreatic cancer) or the symptoms referred to herein for a certain period of time in a subject. It will be understood that the said period of time is dependent on the amount of the drug compound which has been administered and individual factors of the subject. It is to be understood that prevention may not be effective in all subjects treated with the compound according to the present invention. However, the term requires that a statistically significant portion of subjects of a cohort or population are effectively prevented from suffering from a disease or the symptoms referred to herein. Preferably, a cohort or population of subjects is envisaged in this context which normally, i.e. without preventive measures according to the present invention, would develop a disease or symptoms as referred to herein. Whether a portion is statistically significant can be determined without further ado by the person skilled in the art using various well known statistic evaluation tools discussed above. Preferably, prevention shall be effective for at least 60%, at least 70%, at least 80%, or at least 90% of the subjects of a given cohort or population.

The term "migration of cancer cells" as used herein relates to the active movement of cancer cells from the site of the primary tumor to locations elsewhere in the body, preferably from the site of the primary tumor into a blood or lymph vessel and/or out of a blood or lymph vessel into normal tissue. Migration of cancer cells is facilitated e.g. by mesenchymal or amoeboid movement.

The term "inflammatory reaction" as used herein relates to the changes in microenvironment elaborated by normal cells and /or cancer cells in a tissue comprising pancreatic cancer cells, said changes facilitating migration of cancer cells and/or invasion of surrounding tissue by cancer cells. Such changes of microenvironment may comprise, e.g., production of selectins, release of chemokines and/or proteases or the like. Furthermore, said changes in microenvironment may also comprise an increase in blood vessel permeability and/or perfusion. Preferably, the inflammatory reaction is the inflammatory reaction associated with pancreatic cancer.

Moreover, the present invention also relates to a method for the identification of a compound inhibiting CD95 signaling, comprising the steps of a) contacting a cell comprising a functional CD95 signaling pathway with a candidate agent, b) determining the effect on at least one parameter selected from cell proliferation, cell migration, and differentiation, and c) comparing the said effects determined in step b) with the effects observed in the absence of the agent. It is to be understood that the method of the current invention may lead to the identification of candidate inhibitors of CD95 signaling, which need not always be specific inhibitors in the sense that they inhibit a CD95 signaling compound only; e.g. general inhibitors of cellular metabolism may be found. It is known in the art how to identify specific inhibitors from a list of candidate compounds; preferably, specific inhibitors are identified by comparing the modification, preferably phosphorylation, status of CD95 signalling gene products between cells contacted with a candidate compound and cells that were not contacted with said compound and cells that were contacted with a derivative of the candidate compound known to be inactive, see e.g., FIG. 5A. More preferably, the phosphorylation status of Sck and/or an Akt kinase selected from the list consisting of AKT1 kinase (Seq ID NO 21, Genbank Acc No: NP_001014432.1 GI:62241015), AKT2 kinase (Seq ID NO:22, Genbank Acc No: NP_001617.1 GI:4502023), AKT3 kinase isoform 1 (Seq ID NO:23, Genbank Acc No: NP_005456.1 GI:4885549), and AKT3 kinase isoform 2 (Seq ID NO: 24, Genbank Acc No: NP_859029.1 GI:32307163) is determined. Most preferably, it is determined if the compound prevents Sck binding to CD95 (e.g. example 5). Reduced binding can be caused by a compound preventing the two proteins from interacting or by a compound causing the total amount of Sck in the cell to decrease. Furthermore, the method of the current invention can be performed in vivo, e.g. in a non-human animal model of pancreatic cancer (example 7) or in vitro by using cultured pancreatic cancer cells (example 6, FIG. 6). Moreover, determination of the specific binding between Sck and CD95 can be determined in a cell-free system, using cell extracts comprising Sck and CD95.

As used in this specification, the term "contacting" relates to bringing a candidate compound into close proximity to a cell such that the compound can interact with the cell and/or be bound by at least one receptor on the surface of the cell and/or become endocytosed and/or pinocytosed by the cell and/or enter the cell by another route. Preferably, contacting is accomplished by dissolving or dispersing an appropriate amount of the compound in a suitable solvent and mixing the solution or dispersion thus obtained with the culture substrate comprising the cells. It is also contemplated by this specification that the solution or dispersion comprising the candidate compound may comprise other substances, like e.g. transfection agents (e.g. cationic lipids, cationic polymers, or calcium phosphate).

The term "cell comprising a functional CD95 signaling pathway" as used herein relates to a cell comprising the proteins comprised in the CD95 signaling pathway in pancreatic cancer cells as specified above, e.g. CD95, SFK, SHC, Grb2, SOS, and Ras. Preferably, said cell is a pancreatic cancer cell.

The term "candidate compound" preferably relates to a compound suspected to inhibit CD95 signaling in pancreatic cancer cells. Preferably, said candidate compound is a compound suspected to inhibit signaling by CD95, SFK, SHC, Grb2, SOS, or Ras in pancreatic cancer cells. The skilled artisan knows how to adapt the method for the identification of a compound inhibiting CD95 signaling of the present invention to screen chemical or natural compound libraries for candidate compounds. Preferably, highly automated high-throughput systems are used to perform such a screening. More preferably, said candidate compound is an RNAi agent, a ribozyme, a DNAzyme, an inhibitory antibody, or an aptamer inhibiting at least one of the CD95 signaling components as detailed in this specification above.

In another preferred embodiment the present invention relates to a method for the manufacture of a medicament comprising the steps of the method for the identification of a compound inhibiting CD95 signaling and the further step of formulating the inhibiting compound as a medicament as specified herein above.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

FIGURE LEGENDS

FIG. 1: CD95 triggers the PI3K pathway in pancreatic adenocarcinoma cells

The pancreatic cell lines Colo357, PANC1 and the PanD3 primary cell line were incubated with the indicated concentrations of CD95L-T4, Staurosporin (St., 1 µM) and Gemcitabine or left untreated (Co). After 24 h DNA fragmentation was analyzed by FACS (upper panels).

FIG. 2: CD95 triggers the PI3K pathway in pancreatic adenocarcinoma cells

Phosphorylation of AKT and ERK is shown in PanD3, PANC1 and Colo357 cells upon treatment with different concentrations of CD95L-T4 at the indicated time points. P: phosphorylated; T: total.

FIG. 3: CD95 triggers invasion and increased translation in pancreatic adenocarcinoma cells in a FADD-independent manner A) Effect of the PI3K and MEK inhibitors (LY2940092 and PD98059 respectively) on CD95-induced phosphorylation of AKT and ERK is shown in PANC1 and Colo357. Inhibition of PI3K enhances ERK phosphorylation. P: phosphorylated; T: total.

Figure 4:
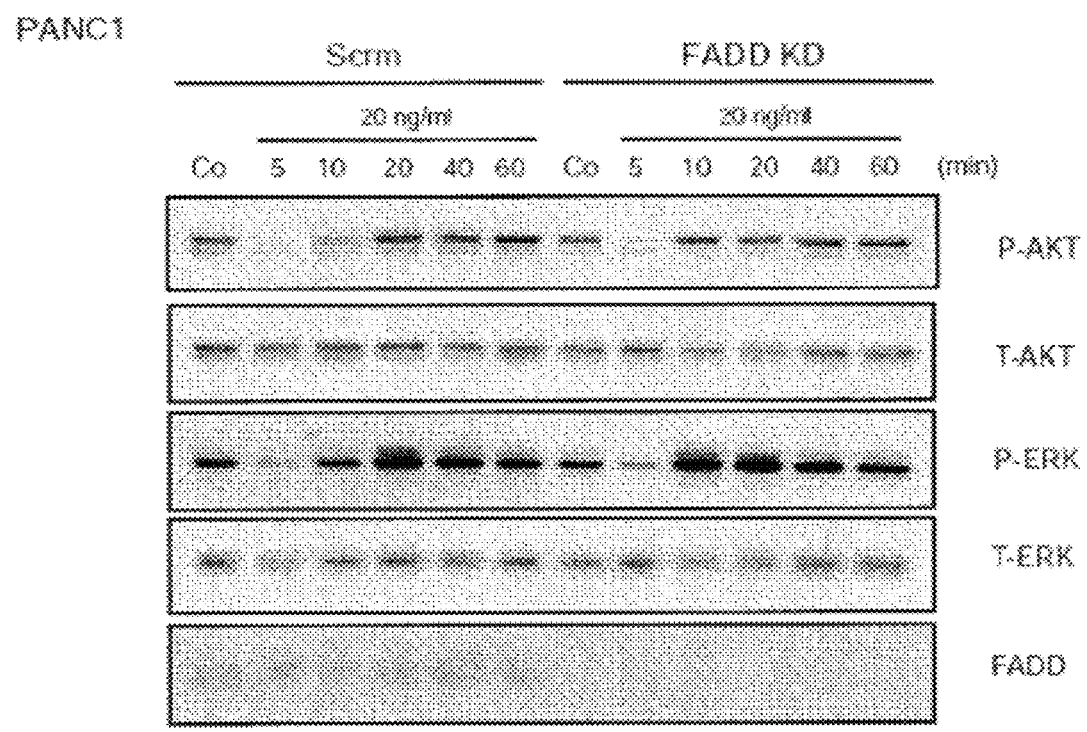

FIG. 4: CD95 triggers invasion and increased translation in pancreatic adenocarcinoma cells in a FADD-independent manner Phosphorylation of AKT and ERK is shown in PANC1 cells upon treatment with CD95L-T4 at the indicated time points under FADD knockdown conditions. P: phosphorylated; T: total.

FIG. 5: CD95 forms a protein complex with the adapter molecule Sck

A) Transignal SH2-domain arrays binding of endogenous CD95 from Colo357, PANC1 and PanD3 to the SH2 of Sck. B) Immunoprecipitation of tyrosine phosphorylated proteins is shown in PANC1 and Colo357. Sck tyrosine phosphorylation increased upon CD95 stimulation. C) Co-immunoprecipitation of CD95 and Sck is shown in PANC1 and Colo357. Increased recruitment of Sck is observed after 15 min stimulation. P: phosphorylated; T: total; *: specific band.

Figure 6:
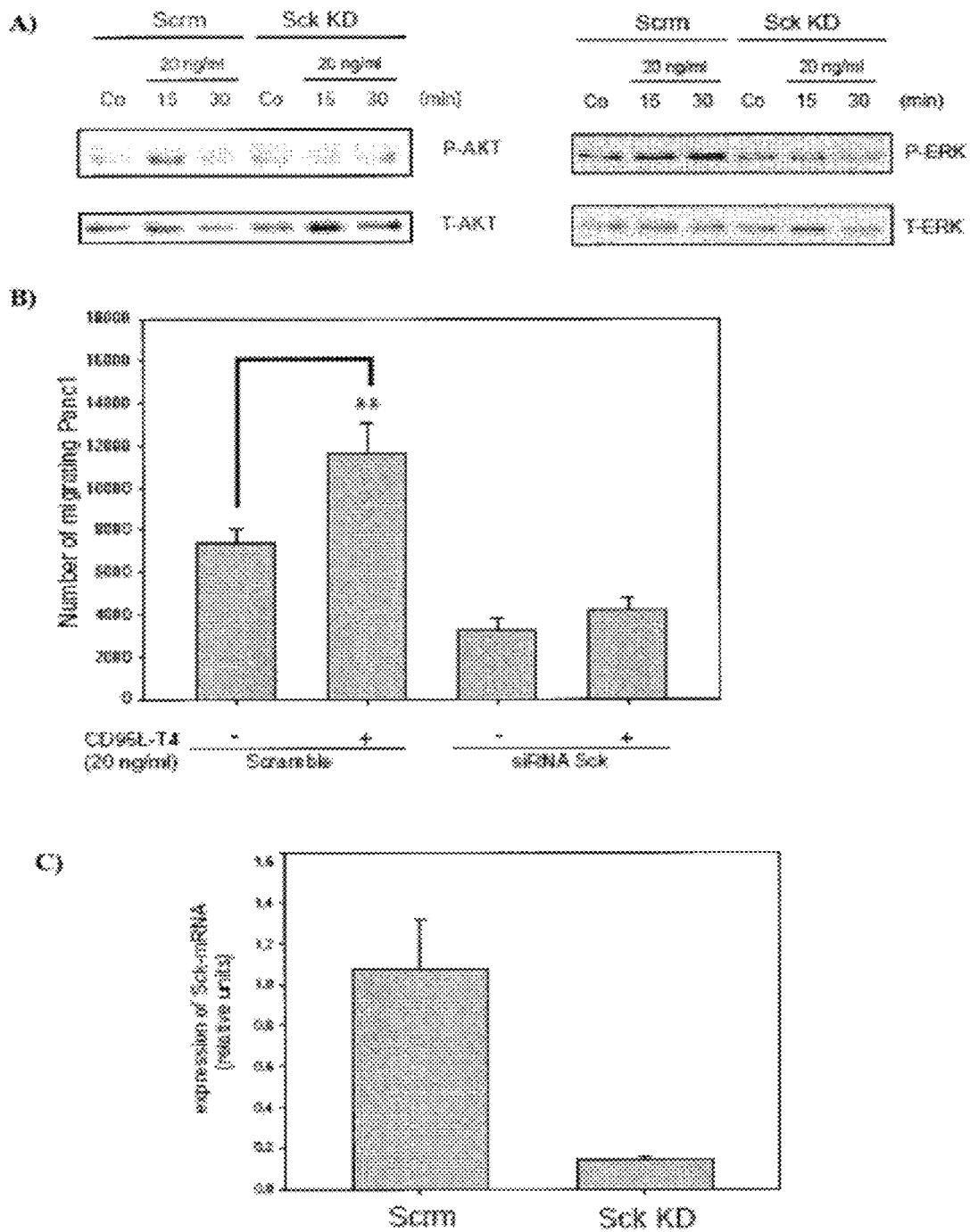

FIG. 6: Sck knockdown abolishes CD95 downstream signaling

A) Sck siRNA blocked CD95-induced phosphorylation of AKT (left panels) and ERK (right panels). B) Sck knockdown abolishes CD95-PI3K induced migration. C) Sck knockdown efficiency assessed by quantitative-RT-PCR is shown. Results are expressed as mean±S.D., **P<0.05

Figure 7:
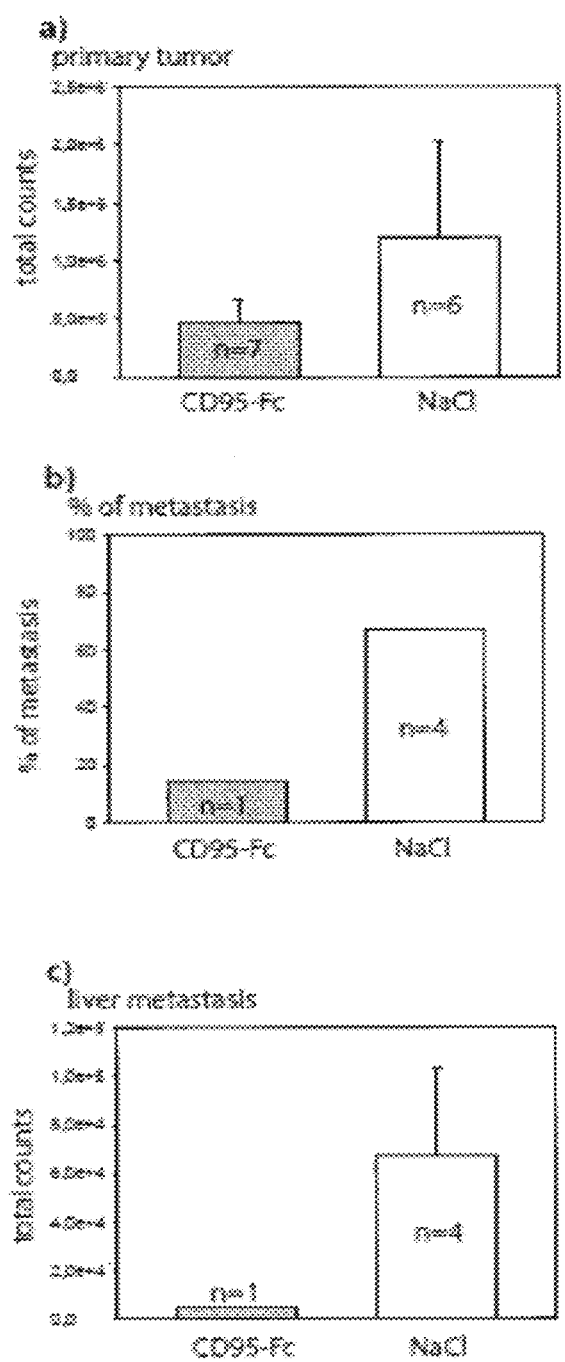

FIG. 7: Neutralizing CD95L in vivo leads to the reduction of tumor volume and metastasis formation a and c) analysis of the bioluminescence intensity by measuring the total photon counts of the primary tumor (a) and the liver metastasis (c) area. b) Percentage of metastasis in the different treatment groups.

EXAMPLES

Example 1

It was studied if the novel roles of CD95 leading to activation of non-apoptotic pathways, such as PI3K, were limited to the Central Nervous System and immune cells. In order to address that hypothesis and extend knowledge on the activation of non-apoptotic pathways by CD95, the system was studied in pancreatic tumour cells. Firstly, different cell lines, PANC1 and Colo357, as well as the stem-like cell line PanD3 were characterized regarding their apoptotic sensitivity. PanD3 cells were isolated from a patient's tumour biopsy and cultured under stem cell conditions. Indeed, PanD3 cells show typical stem cell features such as the ability to form spheres, expression of pancreatic stem-cell markers such as CD24, CD44 and ESA, and moreover a general capacity to form tumours in vivo. PANC1 and PanD3 cells are generally resistant to apoptosis induced by the CD95 system even at high concentrations of the ligand as measured by DNA fragmentation analysis and FACS measurements. On the other hand, Colo357 cells showed high sensitivity to CD95L even at very low concentrations (FIG. 1).

Example 2

It has been known that low concentrations of CD95L are sufficient to efficiently stimulate the non-apoptotic pathways downstream of CD95, being those pathways inhibited by higher concentrations. To assess activation of the previously described non-apoptotic pathways the effect of CD95 stimulation was further characterized by western blotting. CD95 stimulation efficiently activates downstream non-apoptotic pathways such as PI3K and ERK, however several differences could be observed within the different cell systems used in this study. CD95L strongly activates both, the PI3K and ERK pathways in PanD3 and PANC1 whereas activation of PI3K in Colo357 cells was quite subtle (FIG. 2).

Example 3

Interested by the dual-system activation shown by some of the pancreatic cell lines, it was decided to investigate the possible crosstalk between both pathways by comparing the response of Colo357 and PANC1 to different known inhibitors of ERK and PI3K. In this regard, inhibition of PI3K seemed to release a negative feedback loop connecting the PI3K and ERK pathways. Thus, upon inhibition of PI3K, ERK phosphorylation increased in both cell lines. (FIG. 3).

Example 4

Next, FADD knockdown experiments were performed to exclude any involvement in ERK activation of the adapter molecule FADD, the first molecule recruited to CD95 in the molecular cascade of events leading to DISC formation and ultimately apoptosis. In line with previous results, the apoptotic machinery does not seem to be necessary for PI3K and ERK activation as FADD knockdown did not inhibit activation of those pathways. (FIG. 4).

Example 5

Thereafter, the molecular mechanism by which CD95 was able to activate both PI3K and ERK was characterized. To this end, potential adapter proteins ere screened for using SH2 arrays and stimulated cell lysates with the protocol previously established. As shown, CD95 strongly binds the SH2 domain from Sck (FIG. 5A). Sck possesses multiple tyrosine residues able to be phosphorylated, thus immunoprecipitation experiments were performed using a phosphotyrosine specific antibody and subsequently probing the immunoprecipitates with an antibody against Sck. Upon CD95 stimulation, Sck showed an increased phosphorylation of tyrosine residues (FIG. 5B). Moreover, immunoprecipitation of CD95 showed binding of Sck to the CD95 complex, thus defining a novel molecule involved in PAC formation in pancreatic cells (FIG. 5C).

Example 6

Even though co-immunoprecipitation experiments proved physical association of Sck to CD95 and further tyrosine phosphorylation of this adapter protein, it was wondered about the actual role of Sck in signal transduction. To investigate a potential functional role it was decided to perform knockdown experiments and evaluate the phosphorylation of the downstream target of PI3K, AKT. Sck knockdown completely abolished CD95L-induced phosphorylation of AKT (FIGS. 6A and C), thus placing Sck upstream of AKT in the signaling cascade of events. Moreover, Sck KD efficiently blocked CD95L-induced migration of pancreatic cells (FIGS. 6B and C).

Example 7

In Vivo Experiments

Orthotopic injection into the pancreas: All animal experiments were performed in accordance with institutional guidelines of the german cancer research center and approved by the Regierungspräsidium Karlsruhe.

Eight-to-ten week old female C57B16A mice were used for orthotopic implantation of a mouse pancreatic cell line, Panc02, stably infected with a luciferase containing lentiviral vector. In brief, $10^4$ Panc02 cells were injected into the pancreatic head. 3 and 7 days after transplantation the mice were injected i.v. with 50 µg of a neutralizing CD95-Fc protein. Tumours were allowed to grow for 14 days.

Bioluminescence imaging: On day 14, the mice were injected intraperitoneally (i.p.) with luciferin (150 µg/g bodyweight) and placed on the in vivo imaging system (IVIS100; Xenogen). To test whether the mice developed also metastasis in the liver and the lung, they were sacrificed 5 min after the administration of luciferin. The lung and the liver were prepared.

The bioluminescence signals were monitored at 10-s time intervals after 5 min luciferin administration. The signal intensity was quantified as the sum of all detected photon counts within the region of interest after substraction of the measured background luminescence.

Results: Blocking the CD95-system In vivo is reducing tumor volume and metastasis formation To investigate the role of CD95/CD95L in vivo, an orthotopic mouse model of pancreas carcinoma was used. 3 and 7 days post transplantation mice were treated with a CD95L neutralizing Fc-protein. Tumour size and metastasis formation was monitored by bioluminescence imaging technique.

The tumour size was smaller in mice t1reated with CD95-Fc protein compared to the NaCl-treated animals (FIG. 7a). The impact of the CD95-Fc protein on liver metastasis was even higher. Only 16% of the animals in the CD95-Fc protein-treated group showed liver metastasis, which was also smaller in size compared to the NaCl-treated group, where 70% >> of the animals developed liver metastasis (FIGS. 7b and 7c).

Altogether, these in vivo data underscores the importance of the CD95/CD95L-system on tumour formation and metastasis in Pancreatic Ductal Adeno Carcinoma (PDAC).

Example 8

Cell Culture

PanD3 stem-like cells

| Neurobasal A Medium | 500 ml |
| B27 Supplement | 10 ml |
| L-Glutamine | 5 ml |
| Heparin | 500 µl of 2 mg/ml stock (2 µg/ml) |
| bFGF | 20 µl of 0.5 µg/µl stock (20 ng/ml) |
| EGF | 20 µl of 0.5 µg/µl stock (20 ng/ml) |

PANC1 pancreatic cell line

| DMEM | |
| --- | --- |
| F12 supplement | 50% |
| FCS | 10% |

Colo357 pancreatic cell line

| RPMI 1640 | |
| --- | --- |
| FCS | 10% |

Example 9

Knockdown Experiments

Knockdown experiments were performed by transient transfection with Lipofectamine 2000™ (Invitrogen Life Technologies) following the instruction manual. Migration experiments were performed using ON-TARGETplus SMARTpool validated siRNAs against Sck or FADD (Sck, Dharmacon/ThermoFisher, L-031192-00; FADD, DharmaconlThermoFisher, L-003800-00), and a non-targeting pool of siRNAs as a negative control to exclude off-target effects (Dharmacon/ThermoFisher, D-001810-10-05). After transient transfection with the different siRNAs cells were cultured for 72 h before treated with CD95LT4 (20 ng/ml), migration was analyzed 36 h after treatment with a two dimensional migration assay. Knockdown efficiency was controlled by quantitative real-time PCR.

Example 10

SDS PAGE

Determination of Protein Concentration

Protein extraction was performed as previously described. The protein concentration was determined using the BCA protein assay by comparing to standardized concentrations of bovine serum albumin (BSA).

SDS-PAGE

Equal amounts of protein from tissues (20-50 µg depending on the antibody used for detection) in sample buffer were separated by sodiumdodecylsulphate-polyacrylamide gel electrophoresis (SDS-PAGE) on 10-15% polyacrylamide gels. After preparation the polymerization of the gels was initiated by addition of N,N,N,N-tetramethylethylendiamine (TEMED) and ammonium persulphate (APS) solution. The cast running gel was overlaid with distilled water and allowed to polymerize for 30 minutes. Then, the water was removed with filter paper and the stacking gel cast in the same way. Afterwards, the protein samples were loaded and the electrophoresis run at 100V for 30 to 60 minutes.

Example 11

Western Blotting

Proteins were transferred from polyacrylamide gels to nitrocellulose membranes by electroblotting. The gel and the membrane were placed between sheets of absorbent paper and immersed in transfer buffer in an electrophoresis tank. Blotting was performed at 60 mA for 1 to 2 hours at 4° C. Following transfer, non-specific binding sites on the nitrocellulose membrane were blocked by incubation with 5% skim milk powder in PBS-Tween for 1 hour. After washing, the membranes were incubated overnight at 4° C. with primary antibody (usually diluted in PBS-Tween containing 5% skim milk powder) on a shaker. Following thorough washing, antibody binding was visualized via horseradish peroxidase (HRP)-conjugated secondary antibodies, with which the membranes were incubated for 1 hour. The HRP signal was detected by incubation with ECL solution and consecutive exposure to Amersham Hyperfim X-ray films Protein extraction and immunoblotting was performed as previously described. Membranes were probed with the following antibodies: phosphorylated AKT (P-Ser473-AKT, 1:1000, Cell signalling #9271), total AKT (T-AKT, 1:1000, Cell Signalling #9272), FADD (anti-FADD mouse monoclonal Ab, clone 1F7, 1:1000, Millipore #05-486), phosphorylated ERK (P-ERK, 1:1000, Santa Cruz Biotechnologies #sc-7383), total ERK (T-ERK, 1:1000, Santa Cruz Biotechnologies #sc-154), Sck (Sck, 1:1000, Santa Cruz Biotechnologies #sc-33807), and anti-phosphotyrosine, clone 4G10 (pY, 1:1000, Upstate/Millipore 05-321).

Blot Stripping

For removal of antibody complexes from nitrocellulose membranes, membranes were subjected to three washes with 1M Glycine pH 1,8. After thorough washing with PBS-Tween, and blocking unspecific binding sites membranes were reprobed as described above.

Example 12

Immunoprecipitation

At least $1 \times 10^7$ cells were treated with 20 ng/ml of CD95L-T4 for the indicated time at 37° C. or left untreated, washed twice in PBS plus phosphatase inhibitors (NaF, NaN3, pNPP, NaPPi, β-Glycerolphosphate, 10 mM each and 1 mM orthovanadate), and subsequently lysed in buffer A [(20 mM Tris/HCl, pH 7.5, 150 mM NaCl, 2 mM EDTA, 1 mM phenylmethylsulfonyl fluoride, protease inhibitor cocktail (Roche), 1% Triton X-100 (Serva, Heidelberg, Germany), 10% glycerol, and phosphatase inhibitors (NaF, NaN3, pNPP, NaPPi, β-Glycerolphosphate,10 mM each and 1 mM orthovanadate)]. Protein concentration was determined using BCA kit (Pierce). 500 µg of protein was use as input and the desired protein immunoprecipitated overnight with the respective antibodies, 40 µl protein-A Sepharose and the corresponding isotype controls. Beads were washed 5 times with 20 volumes of lysis buffer. The immunoprecipitates were mixed with 40 µl of 2× Laemmli buffer and analysed on 10% SDS-PAGE. Subsequently, the gels were blotted as described on the western blotting section.

Example 13

Detection of Apoptosis (Nicoletti Assay)

To quantify DNA fragmentation, cells detached with trypsin/EDTA (Gibco) were centrifuged at 200×g and fixed with 70% ethanol at −20° C. for 1 h. Fixed cells were stained with propidium iodide solution (50 µg/ml; 0.0025% sodium citrate and 0.0025% Triton-X-100) for 1h or overnight at 4° C. and analyzed by FACS.

Example 14

SH2 Array

The Transsignal SH2 Domain Array (Panomics) was performed according to the manufacturers' instructions. For hybridisation of whole cell lysates, cells were harvested as described above. Lysates were then incubated with 5 µg anti-Apo1 antibody and subsequently hybridised to the SH2-array membrane. After washing the array was incubated with streptavidin-HRP and developed.

Example 15

Migration of Pancreatic Cells

Migration of pancreatic cells was assessed in vitro in a two chamber migration assay. Transwell inserts [8 µm (BD #353097) pore size] were coated with collagen. $1 \times 10^5$ cells were plated in 300 µl medium onto the upper chamber. Cells were left untreated or treated with CD95L-T4 20 ng/ml to the upper chamber. The number of migrated cells was counted 36 hours after treatment.

Example 16

Statistical Analysis

Statistical analysis of migration and mRNA expression data was performed using the non-parametric Student t test to compare differences between treatment groups and controls. Confidence intervals were determined at 95%, and *P values<0.05, P value<0.01 *P value<0.005 were considered statistically significant.

The invention claimed is:

1. A method for treating pancreatic cancer comprising administering to a patient suffering from pancreatic cancer a pharmaceutical composition comprising:
   (a) a compound inhibiting CD95 signaling in a pancreatic cancer cell, wherein the compound is a fusion protein comprising (i) at least one first domain comprising a ligand-binding domain of CD95 fused to (ii) a heterologous second domain comprising at least a portion of a constant immunoglobulin domain; and
   (b) at least one pharmaceutically acceptable carrier;
   wherein in cells of the pancreatic cancer, CD95-signalling is transmitted via interaction of CD95 with Src Homology-2 Domain Containing Transforming Protein.

2. The method of claim 1, wherein there is at least one amino acid overlap between the first domain and the second domain in the fusion region.

3. The method of claim 1, wherein the compound is CD95-Fc.

4. The method of claim 1, wherein the patient is suffering from Pancreatic Ductal Adenocarcinoma (PDAC).

* * * * *